(12) United States Patent
Shigematsu et al.

(10) Patent No.: US 7,419,818 B2
(45) Date of Patent: Sep. 2, 2008

(54) ORGANIC CONDUCTOR

(75) Inventors: Taishi Shigematsu, Minamiashigara (JP); Kei Shimotani, Ashigarakami-gun (JP); Chikara Manabe, Ashigarakami-gun (JP); Hiroyuki Watanabe, Ashigarakami-gun (JP); Masaaki Shimizu, Ashigarakami-gun (JP)

(73) Assignee: Fuji Xerox Co., Ltd, Tokyo (JP)

( * ) Notice: Subject to any disclaimer, the term of this patent is extended or adjusted under 35 U.S.C. 154(b) by 0 days.

(21) Appl. No.: 11/723,330

(22) Filed: Mar. 19, 2007

(65) Prior Publication Data

US 2007/0244309 A1    Oct. 18, 2007

Related U.S. Application Data

(62) Division of application No. 10/325,894, filed on Dec. 23, 2002, now Pat. No. 7,238,794.

(30) Foreign Application Priority Data

Dec. 25, 2001  (JP) ............................. 2001-391420

(51) Int. Cl.
*C12M 1/00*  (2006.01)
(52) U.S. Cl. .................................. 435/283.1
(58) Field of Classification Search ............... 435/283.1
See application file for complete search history.

(56) References Cited

U.S. PATENT DOCUMENTS

| 5,670,621 A | 9/1997 | Donahue et al. |
| 5,714,327 A | 2/1998 | Houthoff et al. |
| 6,114,620 A * | 9/2000 | Zuppero et al. ............. 136/253 |
| 2003/0099684 A1 * | 5/2003 | Domb ........................ 424/426 |

FOREIGN PATENT DOCUMENTS

| EP | 1 209 695 A1 | 5/2002 |
| JP | A-2-11597 | 1/1990 |
| JP | A-2001-64298 | 3/2001 |
| JP | A-2001-294597 | 10/2001 |
| WO | WO 92/01699 | 2/1992 |
| WO | WO 94/22889 | 10/1994 |
| WO | WO 95/26968 | 10/1995 |
| WO | WO 99/31115 | 6/1999 |

OTHER PUBLICATIONS

Richter et al., "Construction of highly conductive nanowires on a DNA template," Applied Physics Letters, vol. 78, No. 4, Jan. 22, 2001, pp. 536-538.
Porath et al., "Direct measurement of electrical transport through DNA molecules," Nature, vol. 403, No. 6770, Feb. 10, 2000, pp. 635-638.
Ford et al. Platinated DNA as Precursors to Templated Chains of Metal Nanoparticles. Advanced Materials, Communications, vol. 13, pp. 1793-1797, Nov. 2001.
Malina et al. Biophysical Journal, vol. 78, pp. 2008-2021, Apr. 2000.
Hofr et al. Nucleic Acids Research, vol. 29, No. 10, pp. 2034-2040, May 2001.
Reedijk, Jan. Pure and Applied Chemistry, vol. 59, No. 2, pp. 181-192, 1987.
Brabec, Nucleic Acids Research, vol. 24, No. 2m, Jan. 1996, pp. 336-341.

* cited by examiner

*Primary Examiner*—Kenneth R. Horlick
*Assistant Examiner*—Cynthia Wilder
(74) *Attorney, Agent, or Firm*—Oliff & Berridge, PLC

(57) ABSTRACT

The present invention provides an organic conductor comprising a deoxyribonucleic acid (DNA) and an electric charge-donating material bonded to the deoxyribonucleic acid, and an organic conductor comprising at least two DNAs; and an electric charge-transfer substance bonding to each base of the two DNAs.

5 Claims, 23 Drawing Sheets

ORGANIC CONDUCTOR

This is a Division of application Ser. No. 10/325,894 filed Dec. 23, 2002 now U.S. Pat. No. 7,238,794. The disclosure of the prior application is hereby incorporated by reference herein in its entirety.

BACKGROUND OF THE INVENTION

1. Field of the Invention

The present invention relates to an organic conductor having an improved DNA conductivity which allows a DNA to be utilized as an electronic material.

2. Description of the Related Art

A deoxyribonucleic acid (DNA) defined by Watson and Crick has a unique double-helix structure consisting of pairs of four bases including adenine, cytosine, guanine and thymine and ribose phosphate chains. Originally, a DNA is a substance, which constitutes a chromosome in a nucleus of an organism, and has a function for replicating and transmitting genetic information of a life by recording main genetic information in the base sequence of a DNA. The error rate in the transcription of a DNA is very low, and is thought to be several thousand times smaller than the error rate of an ordinary magnetic memory disk ($10^{-4}$%). In addition, the thickness of a DNA is only about 2 nm, but a DNA present in a nucleus of a cell has a length of about several meters when being extended and an extremely high dynamic toughness.

Since such a DNA has an almost one-dimensional geometric structure, it is being paid attention also as a low-dimensional transmitting substance. If a DNA can be employed on an electronic circuit, it can serve as a minute circuit element which can achieve an accumulation level exceeding that of a conventional silicon device circuit. Accordingly, the use of a DNA as an electronic device material is increasingly being discussed, and attention is focused particularly on the electric conductivity of the DNA. However, the level at which a DNA allows the electricity to flow is not known accurately, and is presently still being discussed.

As described above, the results of the prior studies have not been successful in determining even whether a DNA is a conductor or not, and no accurate conductivity has been measured. Accordingly, there were no technologies by which the electricity is supplied efficiently to a DNA.

SUMMARY OF THE INVENTION

Accordingly, an object of the present invention is to provide a technology enabling a supply of electricity to a DNA which is essential for realizing an electronic device using the DNA.

According to such condition, the present inventor has studied extensively, and finally discovered that an organic polymer formed by binding an electric charge-donating material to a DNA has a high electric conductivity and is stable chemically and thermally, thereby achieving the invention.

Thus, a first aspect of the invention provides an organic conductor comprising a deoxyribonucleic acid (DNA); and an electric charge-donating material bonded to the deoxyribonucleic acid (DNA).

A second aspect of the invention provides an organic conductor comprising at least two DNAs; and an electric charge-transfer substance bonding to each base of the two DNAs.

An organic conductor of the invention allows a DNA for the first time to have a conductivity, and enables the realization of an electric charge separation state in a single molecule, which is very useful industrially for the purpose of actuating a molecular level electronic device.

DETAILED DESCRIPTION OF THE PREFERRED EMBODIMENTS

Figure 1:
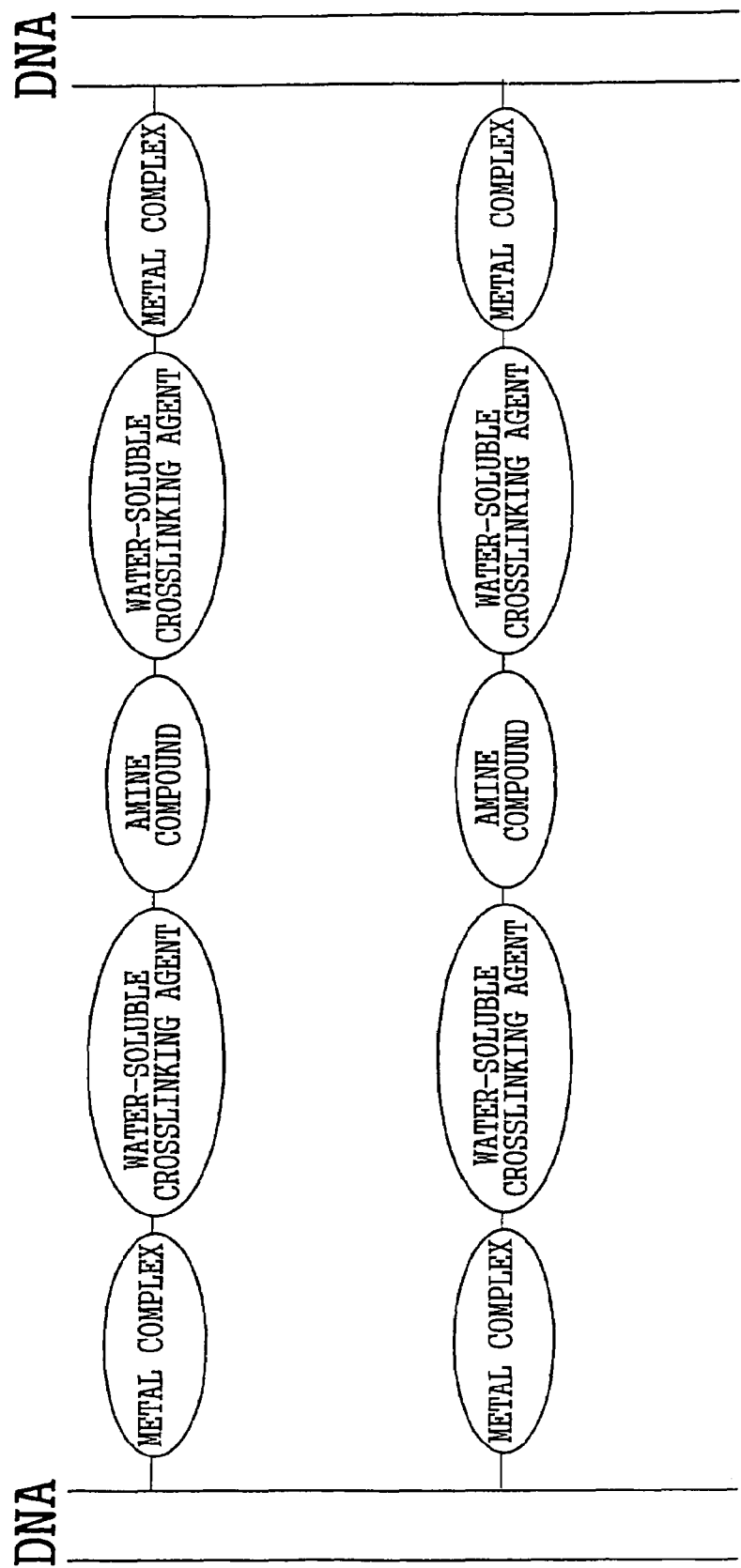
FIG. 1 is a diagram showing an example of the structure of the present invention.

The present invention is a DNA imparted with an electric conductivity by binding it with an electric charge-donating material. The DNA employed in the invention is not limited particularly, and may be any of a single-stranded to quadruple-stranded DNAs and also may a DNA having a trifurcate or tetrafurcate branching structure. While the number of the bases is not limited, it is preferably 2 to 100,000.

An electric charge-donating material employed in the invention serves to inject a hole or an electron into a DNA. Since the electric charge-donating material employed here bonds to the DNA, it is preferable that the electric charge-donating material bonds specifically to a base of the DNA. While an electric charge-generating substance itself serves as an electric charge-donating material if the electric charge-generating substance bonds directly to a base, the electric charge-donating material preferably contains an electric charge-transfer substance capable of bonding to a base and an electric charge-generating substance when it is difficult for the electric charge-generating substance to bond directly to the base.

When an electric charge-donating material bonds specifically to a desired base of a DNA, then the conductivity can be controlled based on the base sequence constituting a DNA and the bonding site between DNAs and the number of the bondings can also be controlled. For example, a cis-platin-containing electric charge-donating material described below bonds specifically to guanine, whereby enabling the control as mentioned above. The DNA employed here may be a naturally occurring one whose sequence, number or base position is known to a certain degree required for its utilization, or may be an artificial one whose sequence is designed.

An electric charge-transfer substance employed in the invention is a substance capable of transmitting a hole or electron generated in an electric charge-generating substance to a DNA. The electric charge-transfer substance may for example be a metal complex, and preferably a platinum complex. Such a platinum complex is preferably a carcinostatic platinum complex (cis-platinum (II) diamine dichloride (hereinafter abbreviated as cis-platin), cis-[Pt(NH$_3$)$_2$Cl$_4$], trans-DDP, [Pt(dien)Cl]$^+$, carboplatin, CHIP (iproplatin), DACCP, malonatoplatinum and the like as shown below.

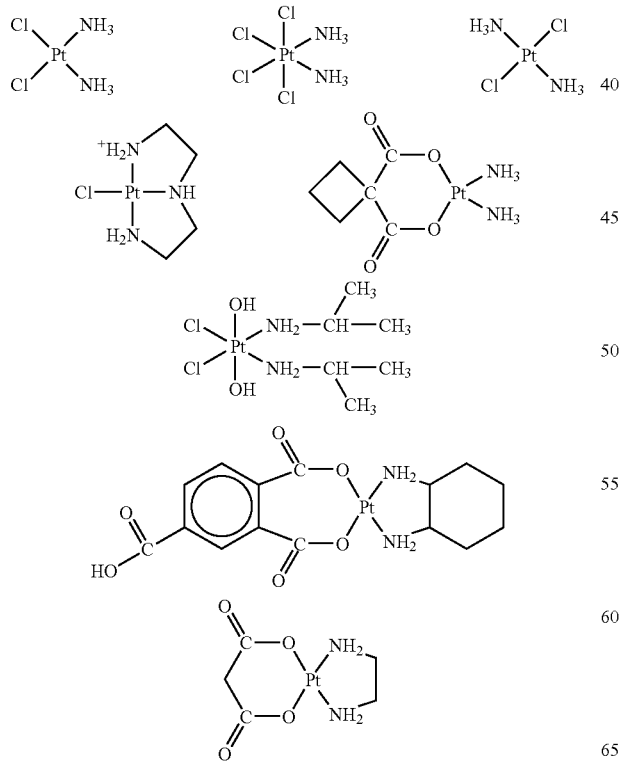

An electric charge-generating substance may, for example, be an amine compound, particularly one in which the number of amine groups is 1 to 100 per molecule of the amine compound, and more preferably a water-soluble amine. Those preferred particularly are CONGO RED, pararosanilin, thionine, porphyrin and the like as shown below.

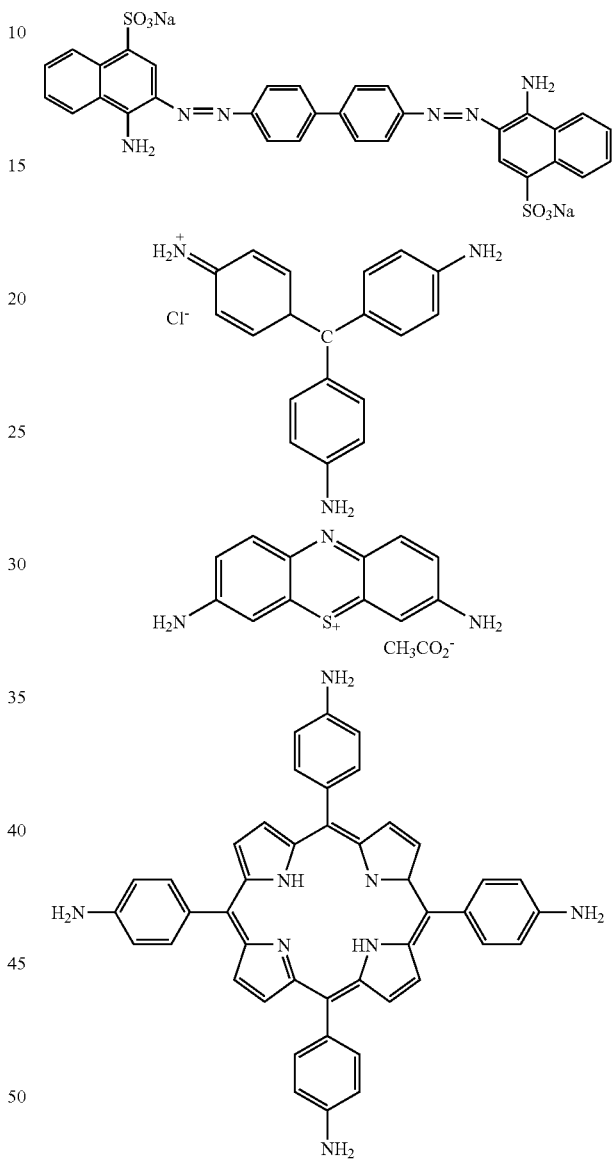

When an electric charge-transfer substance capable of bonding to a base cannot be bonded directly to an electric charge-generating substance, then they may be bonded to each other via a crosslinking agent. Such a crosslinking agent is preferably a water-soluble crosslinking agent, particularly a water-soluble isothiocyanate represented by Formula 1 (4,4'-diisothiocyano-2,2'-stilbenedisulfonic acid disodium salt (hereinafter abbreviated as DIDS), 4-acetamido-4'-isothiocyanostilbene-2,2'-disulfonic acid disodium salt and the like), succinic acid imide ester represented by Formula 2 (ethylene glycol-O,O'-bis(succinimidyl) succinate (hereinafter abbreviated as EGS).

Formula 1

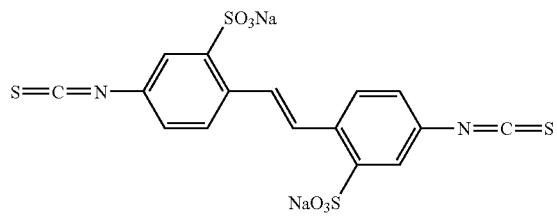

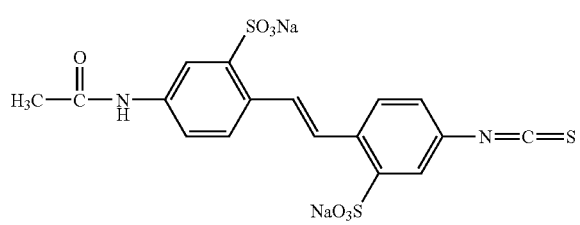

Formula 2

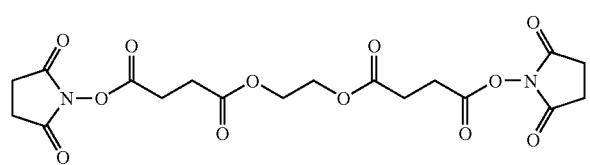

While an organic conductor of the invention may be in a form obtained simply by binding an electric charge-donating material to a deoxyribonucleic acid (DNA), it may be in a form in which 2 or more DNAs are crosslinked with the electric charge-donating material. Thus, the form may be DNA-electric charge-donating material-DNA, or a repeating structure such as DNA-electric charge-donating material-DNA-electric charge-donating material-DNA-. The number of DNAs in such a crosslinking structure may be 2 to 100,000.

The invention is further detailed by exemplifying an inventive organic conductor having a crosslinking structure. This has a structure shown in FIG. 1. The characteristics of the chemical substance can be obtained in such a mannar that a guanine base of a DNA is bonded to a metal complex, preferably the above-described carcinostatic platinum complex (cis-platin, cis-[Pt(NH$_3$)$_2$Cl$_4$], trans-DDP, [Pt(dien)Cl]$^+$, carboplatin, CHIP (iproplatin), DACCP, malonatoplatinum and the like), followed by a thiourea bond formation using a water-soluble crosslinking agent, preferably a water-soluble isothiocyanate represented by Formula 1 (DIDS, or 4-acetamido-4'-isothiocyanostilbene-2,2'-disulfonic acid disodium salt and the like) or an amide bond formation using EGS represented by Formula 2, via which an electric charge-generating substance such as an amine compound, preferably a water-soluble amine, particularly CONGO RED, pararosanilin, thionine, porphyrin and the like described above is bonded to the DNA.

Figure 2:
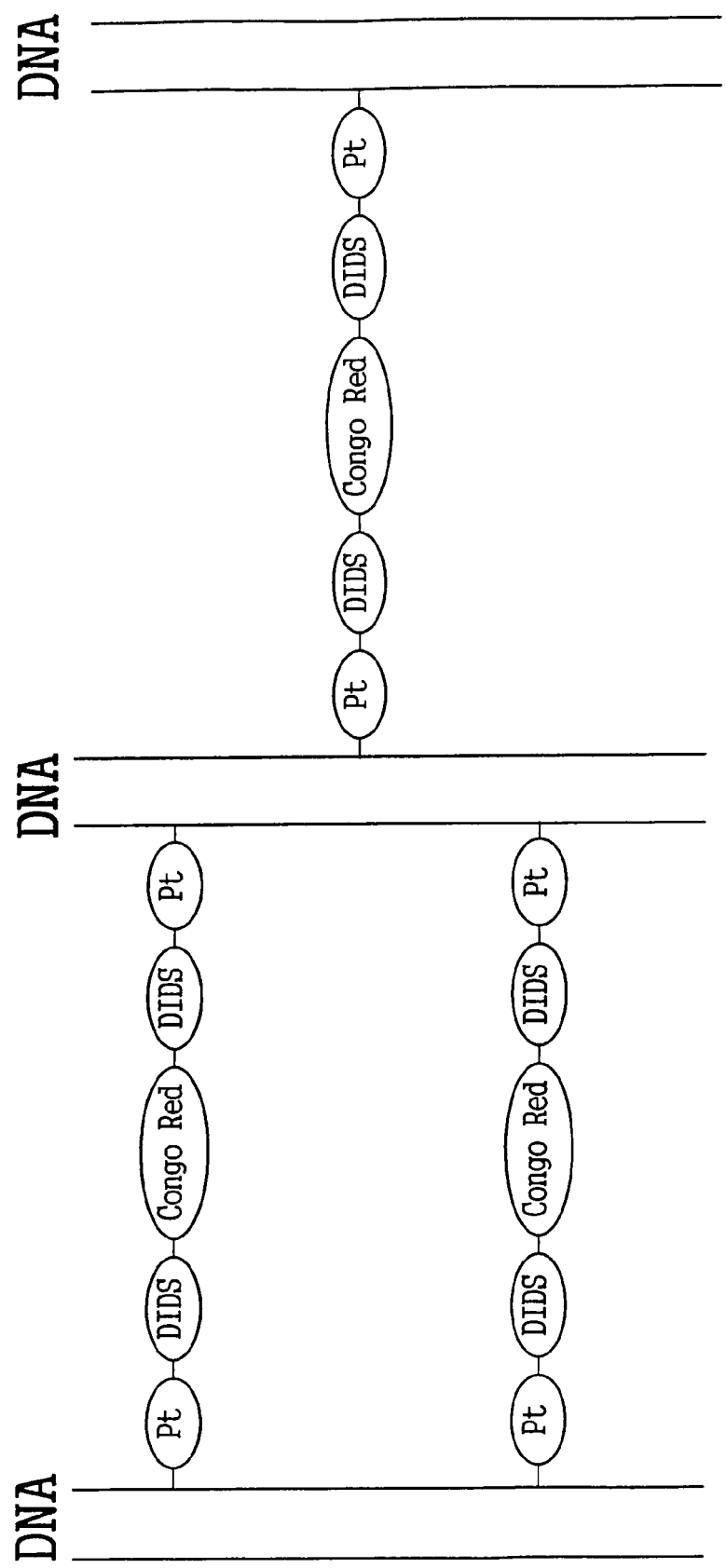
FIG. 2 is a diagram showing an example (A-1) of the structure of the invention.

A further description is made below with exemplifying a substance DNA/cis-platin/DIDS/CONGO RED/DIDS/cis-platin/DNA (hereinafter abbreviated as A-1) (see FIG. 2). When a DNA is reacted with cis-platin, the chlorine on cis-platin is cleaved to form a bond at the N7 position of a guanine base of the DNA (Formula 3). Subsequently, —NH$_3$ of cis-platin and N═C═S group (thioisocyanate group) of DIDS are reacted to form a thiourea bond (Formula 4). At the same time, CONGO RED, which can form a similar thiourea bond, is reacted (Formula 5), whereby producing A-1 shown above (Formula 6).

Formula 3

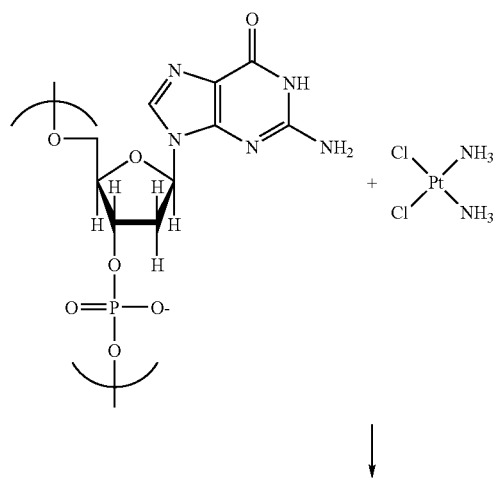

-continued
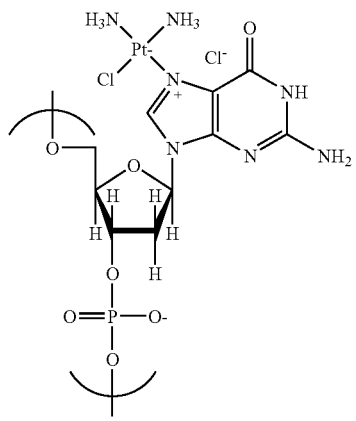
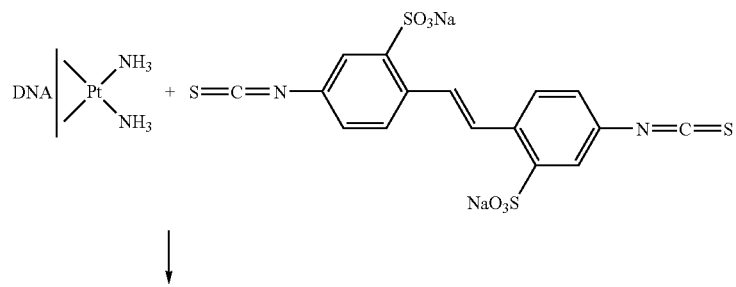
Formula 4
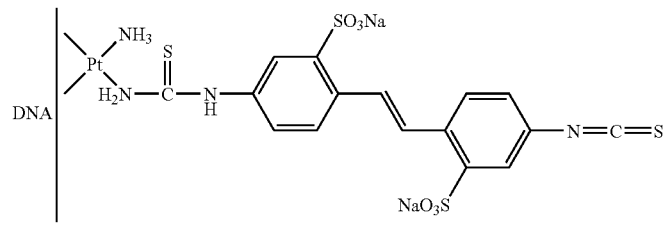
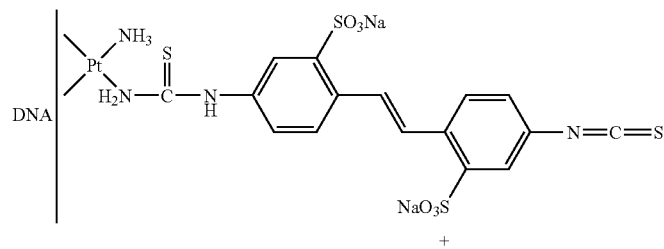
Formula 5
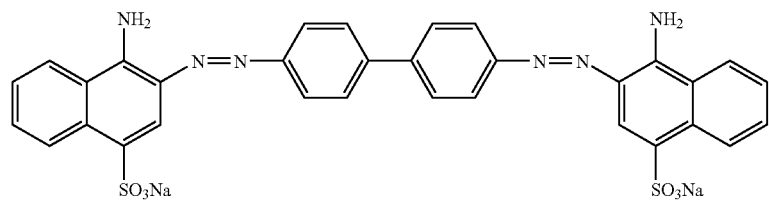

-continued

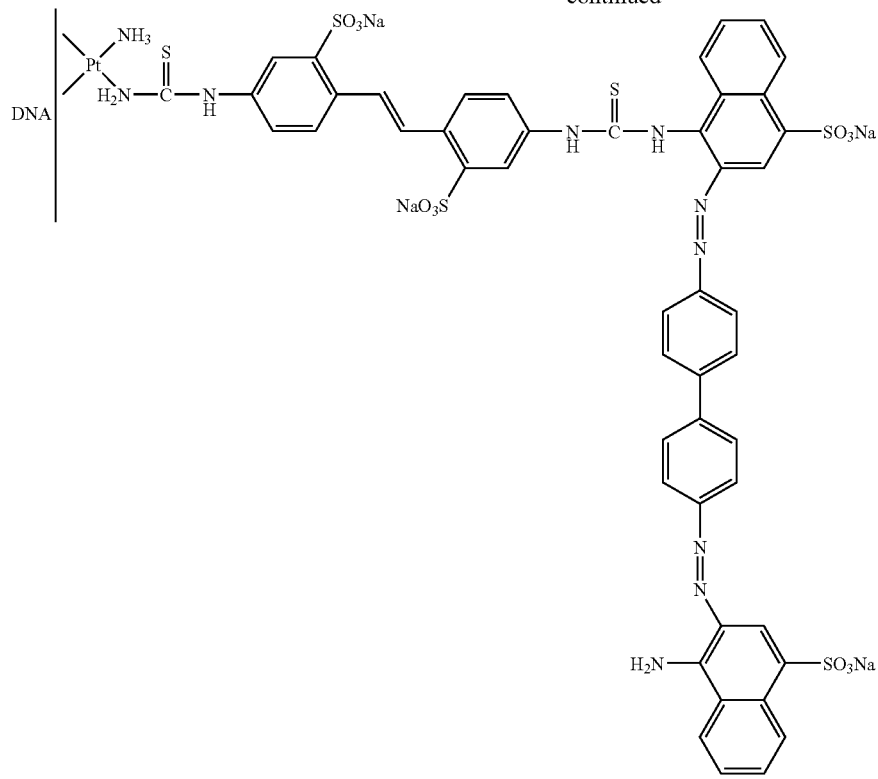

Formula 6

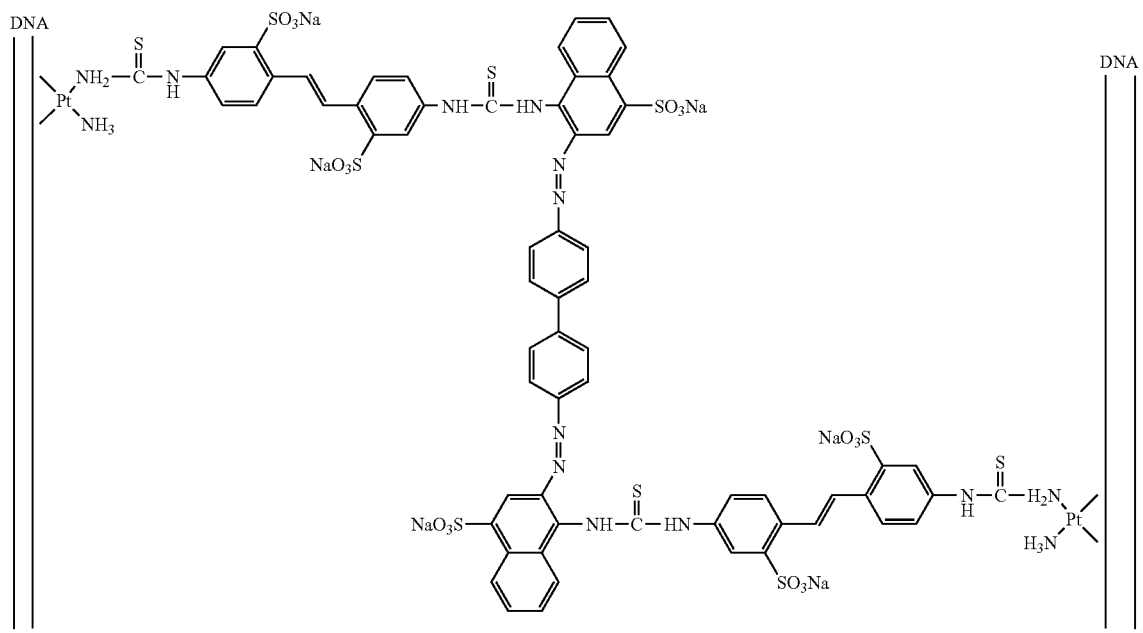

This substance allows the electric charge to be separated in a CONGO RED molecule to form a hole which is transmitted by the conjugated double bond and a phenyl group in DIDS, followed by an injection of the hole specifically to a guanine group of a DNA by means of cis-platin bonded to the guanine base of the DNA, whereby accomplishing the transmission of the hole in the DNA molecule chain. The reasons why the hole can readily be injected at the guanine base site of the DNA is the fact that the oxidation potential of the guanine is lower than those of other three bases (adenine, cytosine, thymine). The oxidation potential of each base, relative to hydrogen electrode potential, is 1.49 V for guanine, 1.96 V for adenine, 2.14 V for cytosine, 2.11 V for thymine as reported by C. A. M. Seidel et al. (Journal of Physical Chemistry, vol. 100, pp. 5541 to 5553, 1996, p. 5544, Table 2). As a result, the conductivity of the substance of the invention can be improved.

Generally, the electric resistance of a DNA is extremely high, and the conductivity cannot be dramatically improved even if an organic dye or the like capable of generating an electric charge in a molecule is intercalated. Nevertheless, it can be interpreted that when a hole is injected specifically to a guanine base to increase the electric charge concentration in the DNA then the electric charge in the DNA is transferred, whereby allowing the current to run more easily. On the other hand, when the electric charge is an electron, the electron is injected into cytosine or thymine.

Since A-1 has two bonding sites which are equivalent for all molecules and which are also symmetrical chemically, it can form a complicated crosslinking structure using a DNA as a backbone chain. Thus, a structure: DNA/cis-platin/ DIDS/ CONGO RED/DIDS/cis-platin/DNA can be considered. Such a structure allows the thermal resistance of the substance to be improved to give a thermal decomposition temperature as high as about 450° C. or higher under nitrogen atmosphere, whereby having an extremely high chemical stability.

On the other hand, an ordinary conductive polymer such as a polyacetylene or polypyrrole becomes instable readily by an atmospheric oxidation, and requires a chemically instable iodine and the like as a dopant for generating the conductivity. On the contrary, A-1 of the invention does not require a dopant for generating the conductivity, is stable under atmosphere, and exhibits no change in the characteristics even after being allowed to stand at room temperature under atmosphere for 1 month after production.

It is a matter of course that a substance forming no crosslinking structure can also be considered, such as a DNA/cis-platin/DIDS bonded at its tip to a monoamine dye, in which no crosslinking structure is formed and a fibrous DNA structure is preserved. The reaction is not limited to a reaction only with DNAs, and a DNA molecule can be bonded to a protein molecule via cis-platin/DIDS/(diamine compound)/DIDS/.

Since CONGO RED has an absorption wavelength of about 570 nm and gives almost no fluorescence, it can be employed also as an electric charge-generating material. Accordingly, the synthesized A-1 can constitute an extremely stable photosensor. In addition, CONGO RED is a dyeing agent which stains an amyloid protein specifically, and the synthesized A-1 can be employed also as an electronic sensor which detects many amyloid proteins having β sheet structures (β type prions).

A structure in which 2 or more DNAs are bonded via an electric charge-transfer substance capable of bonding to a base or a structure in which such an electric charge-transfer substance capable of bonding to a base is bonded via a crosslinking agent has been proven to have a conductivity higher than that of a DNA itself. The electric charge-transfer substance and the crosslinking agent mentioned here are similar to those described above. Those which can be exemplified include a substance having a DNA/cis-platin/DIDS/cis-platin/DNA structure, which forms a crosslinking structure and has a conductivity higher than that of a DNA itself.

EXAMPLES

The invention is further described in the following Examples which are not intended to restrict the invention.

Example 1

Figure 3:
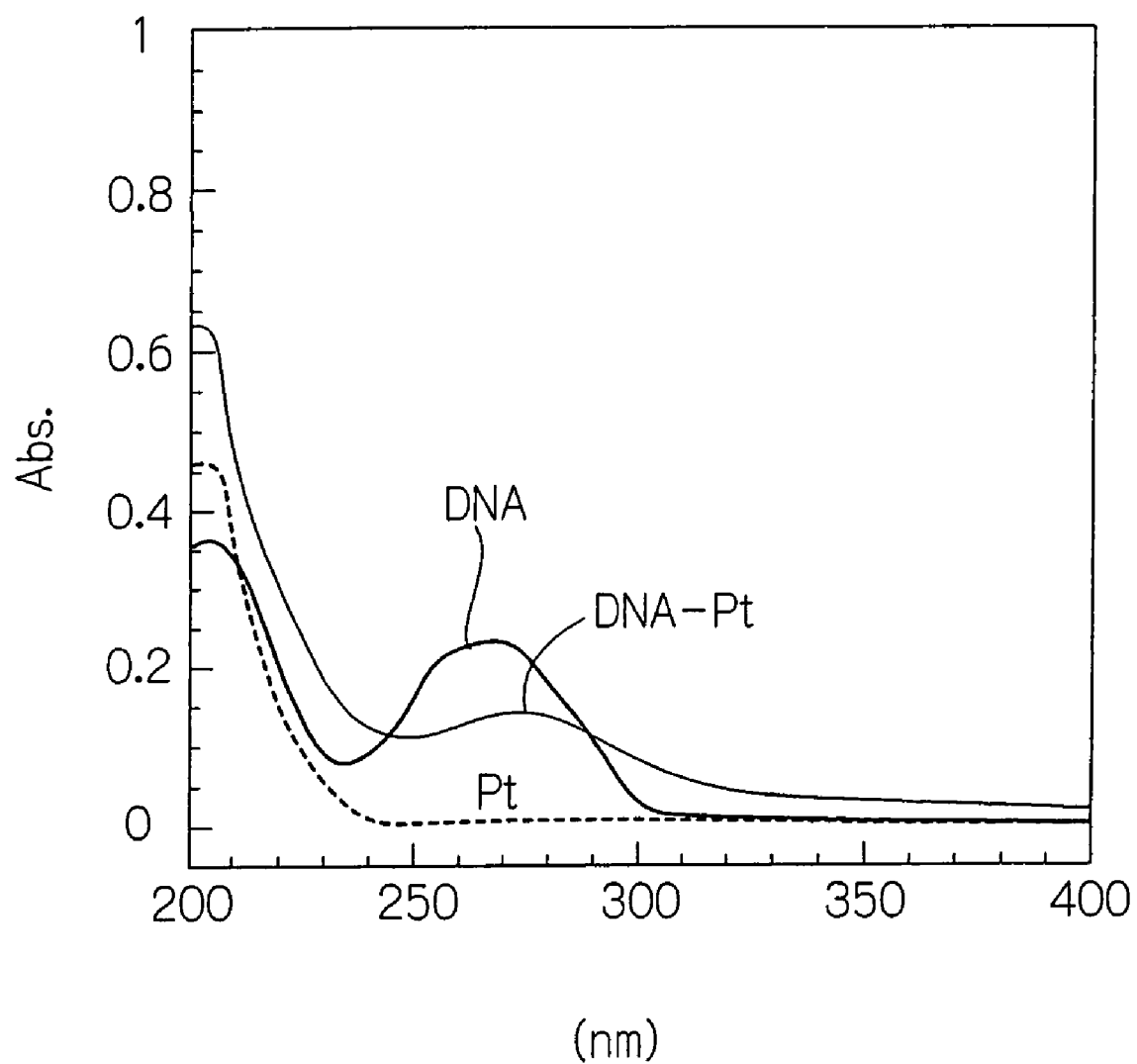
FIG. 3 shows the UV and visible light absorption spectra before and after the reaction of a DNA and cis-platin.
Figure 4:
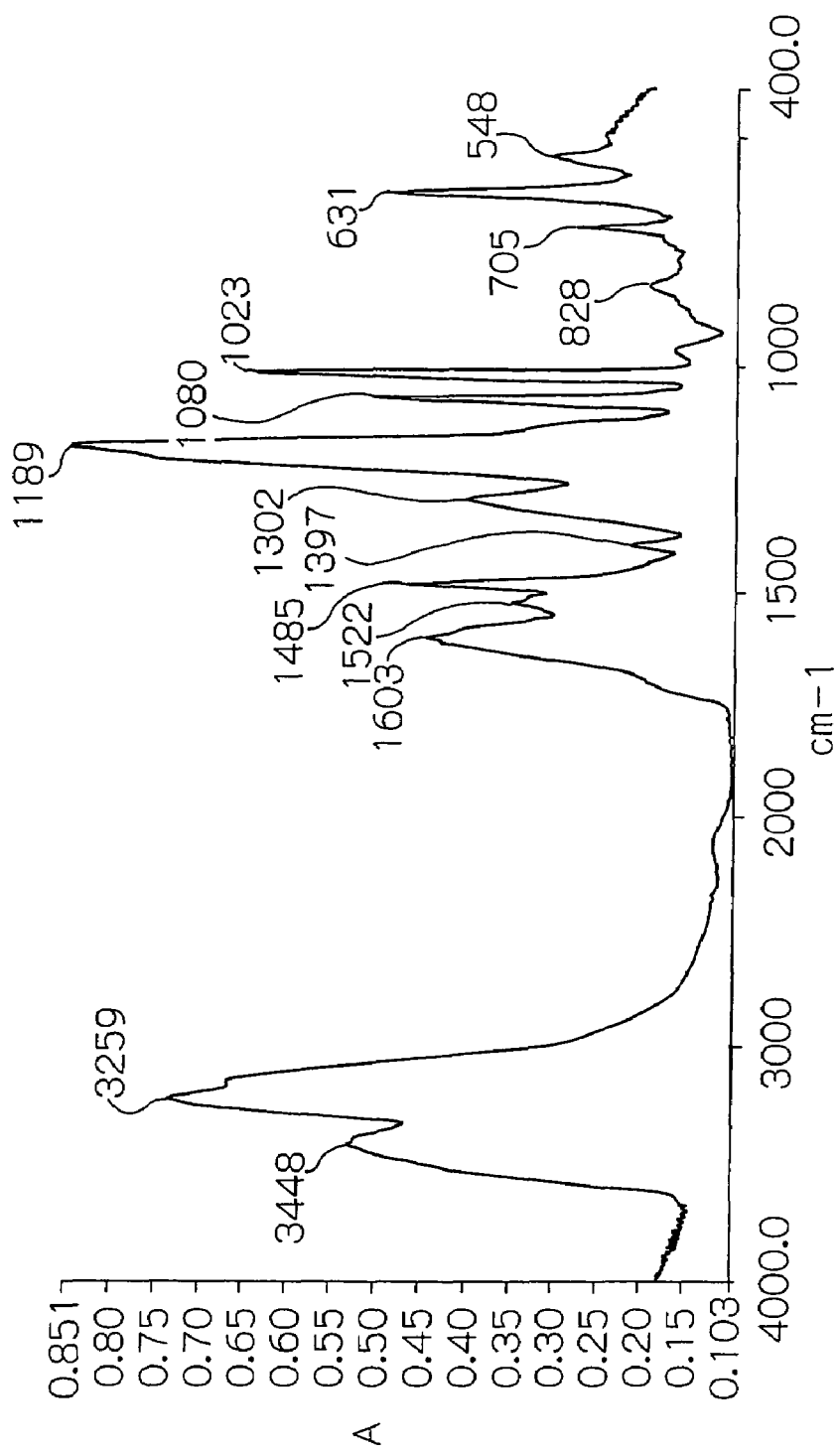
FIG. 4 shows the infrared spectrum of a reaction product of cis-platin and DIDS.
Figure 5:
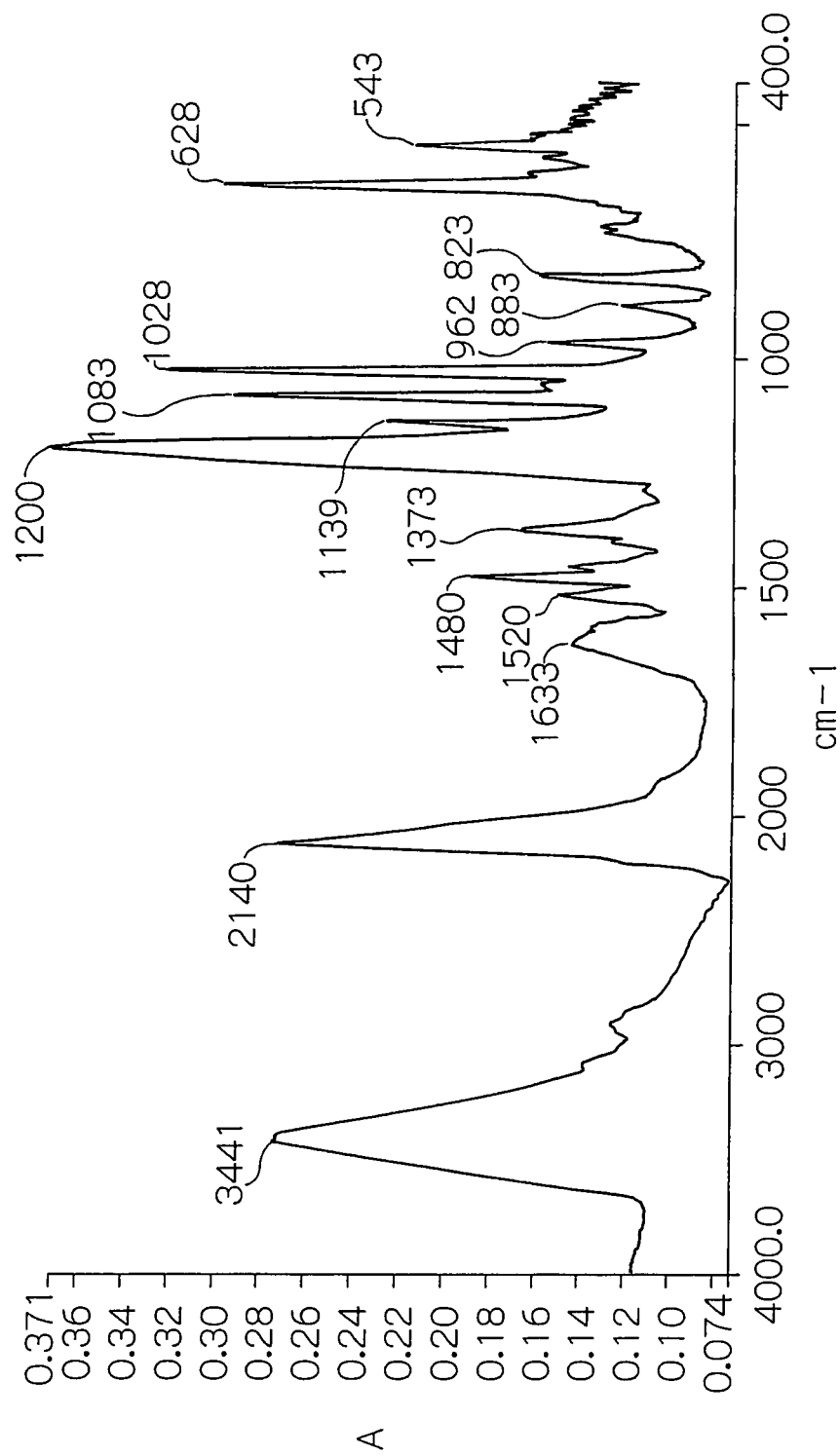
FIG. 5 shows the infrared spectrum of DIDS.
Figure 6:
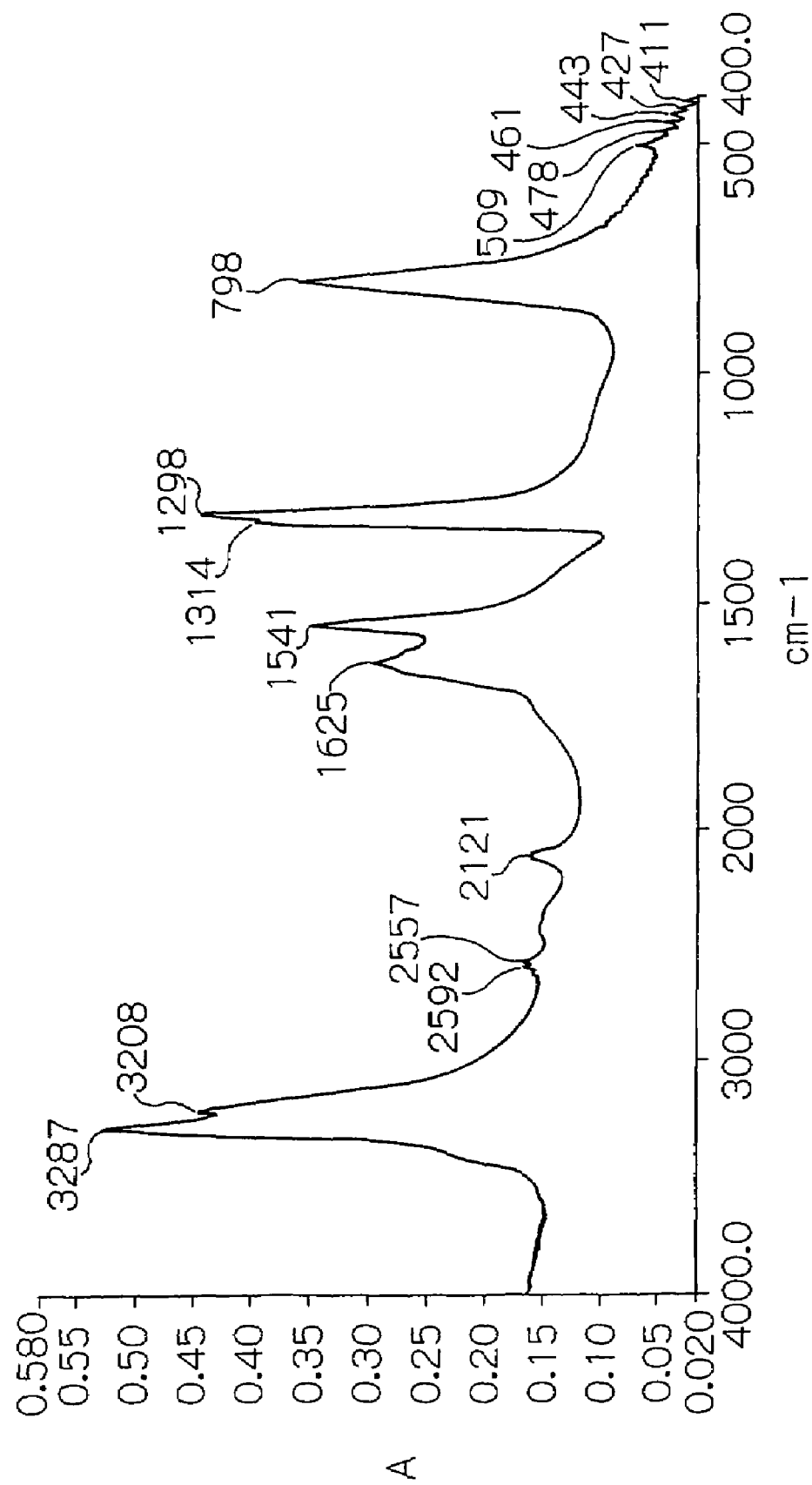
FIG. 6 shows the infrared spectrum of cis-platin.
Figure 7:
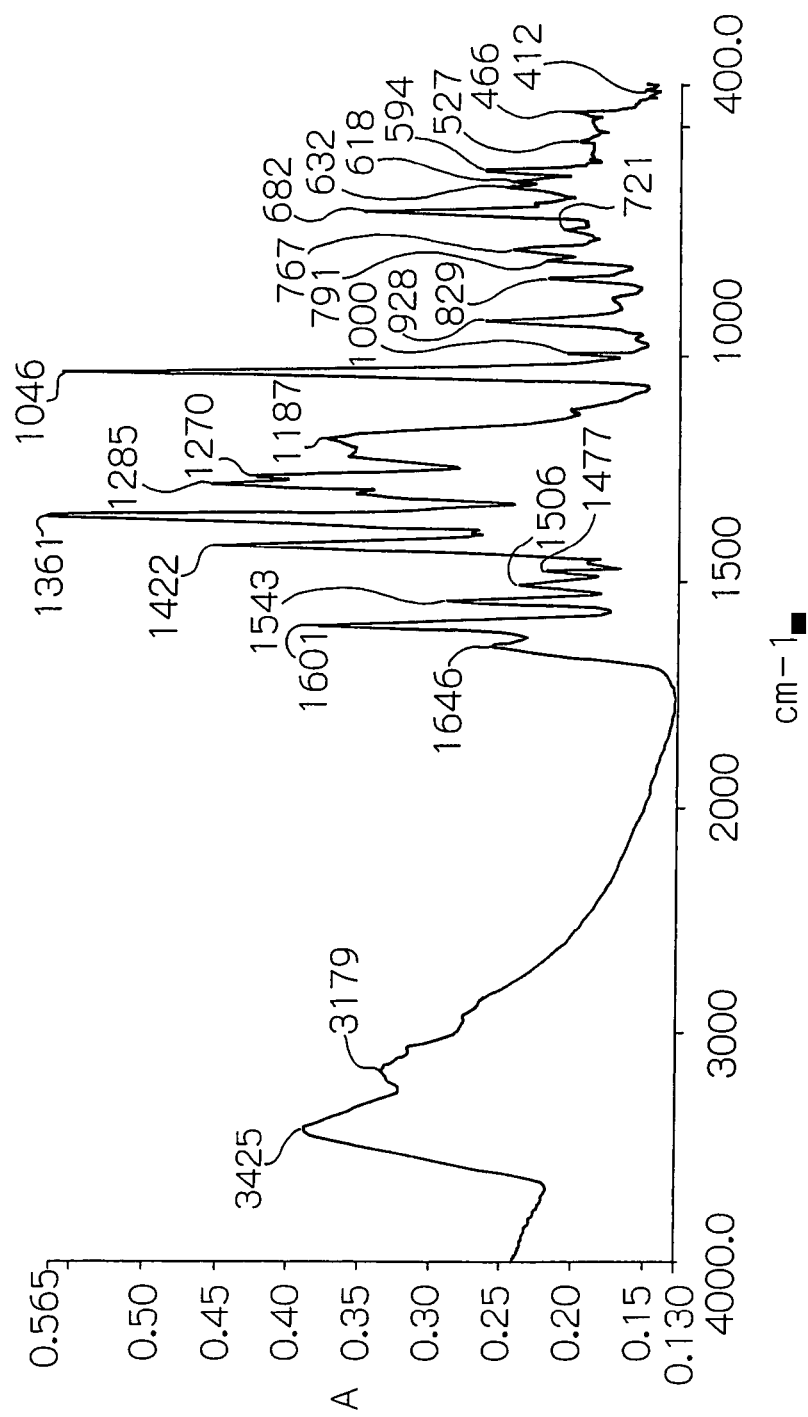
FIG. 7 shows the infrared spectrum of the reaction product of DIDS and CONGO RED, an azine dye indicator.
Figure 8:
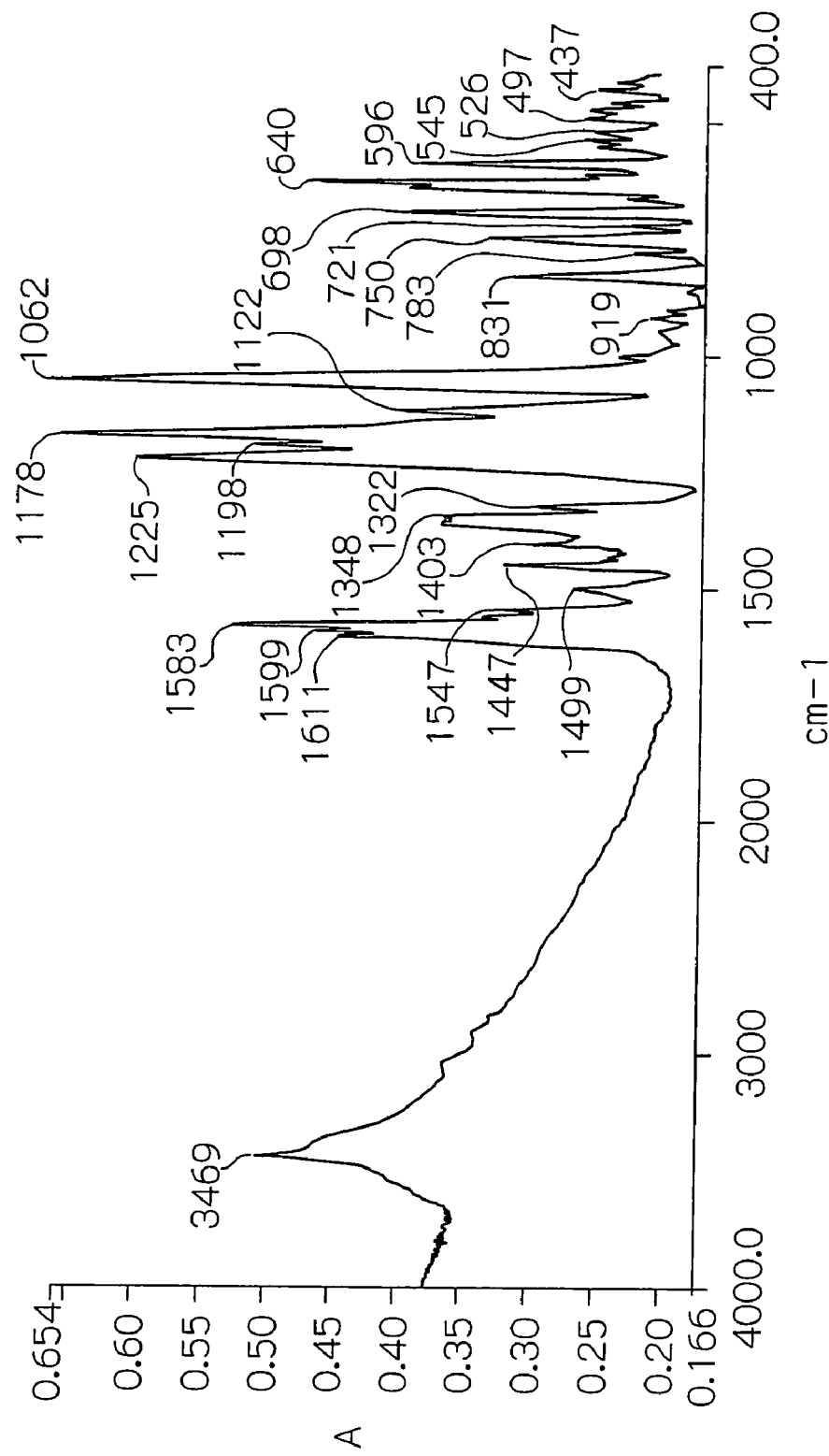
FIG. 8 shows the infrared spectrum of CONGO RED.
Figure 9:
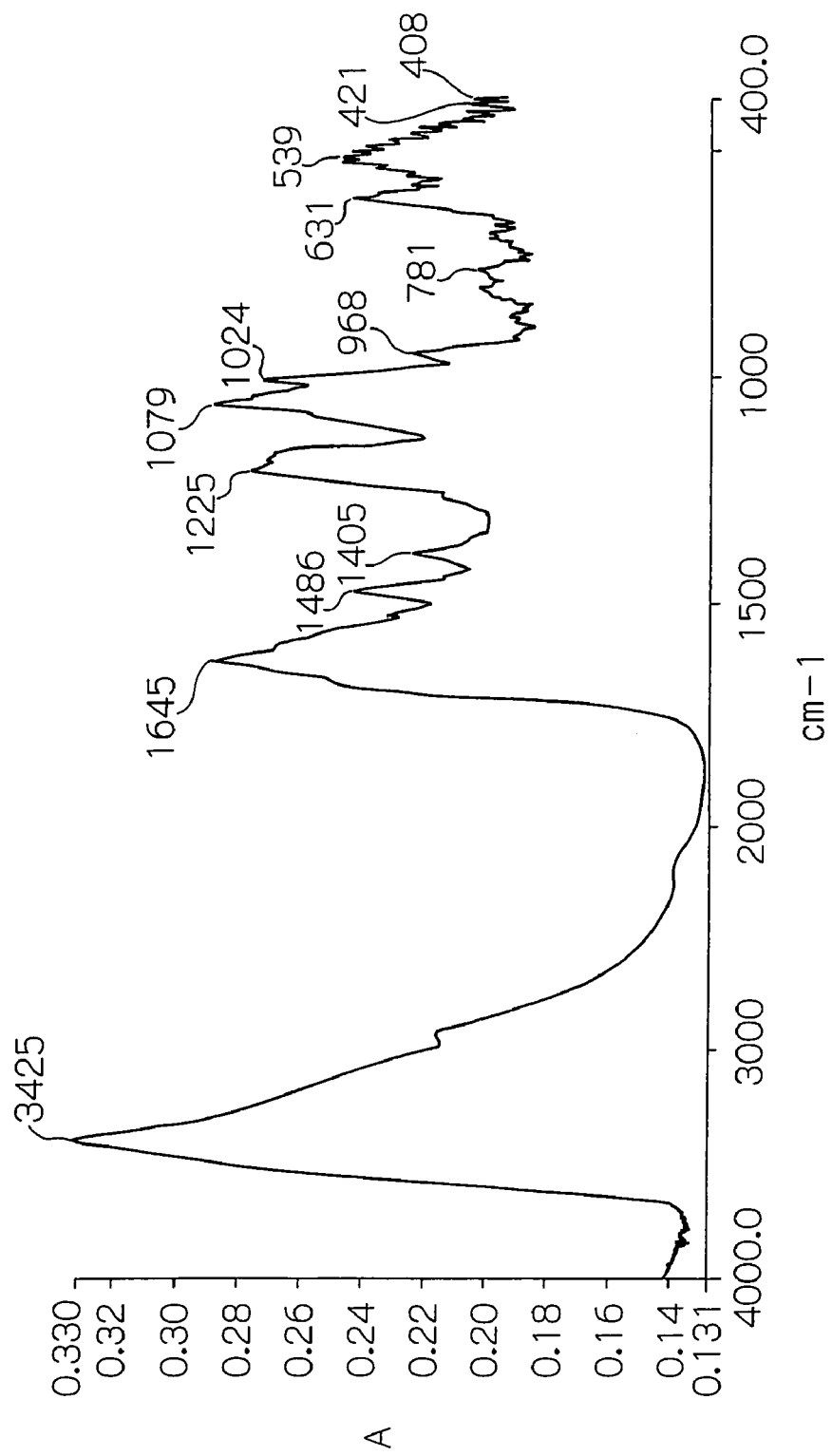
FIG. 9 shows the infrared spectrum of the reaction product of a DNA, cis-platin, DIDS and CONGO RED.

The water employed was a super-pure water (having a resistance of $10^{18}\Omega$ or higher) obtained by purification using a super-pure water producing instrument MILLIQ manufactured by MILLOPORE. The DNA employed was a bacteriophage $\lambda cl_{857}$ Sam7-derived λDNA (TAKARA SHUZO Co., Ltd.). The λDNA was dissolved at 0.4 mg/ml in a TE buffer (Tris: 10 mM, EDTA: 1 mM, pH=8). First, 1 ml of the λDNA buffer solution was mixed with 80 μl of a 2.5 mg/ml aqueous solution of cis-platin (Sigma-Aldrich Co.). Then 301 μl of a 1 mg/ml aqueous solution of DIDS (DOJINDO LABORATORIES) and 400 μl of a 0.5 mg/ml aqueous solution of CONGO RED (Wako Pure Chemical Industries, Ltd.) were added to the resultant mixture, and the mixture was kept at 55° C. for 3 days. The formation of the crosslinked construct represented by Formula 6 was identified on the basis of the results described below. A naturally occurring DNA has the maximum absorption wavelength of 260 nm in a UV and visible light absorption spectrum, but it is known to undergo an about 10 nm red shift of the maximum absorption wavelength when a Pt complex is bonded (Journal of the American Chemical Society, 1980, Vol. 102, pp. 5565 to 5572, Chottard et al., p. 5567, left column, line 8 from the bottom). FIG. 3 shows the UV and visible light absorption spectrum when a DNA was reacted with cis-platin. As evident from FIG. 3, the DNA itself exhibited the maximum absorption at 260 nm, while that when reacted with cis-platin exhibited the maximum absorption at 270 nm. Thus, the maximum absorption wavelength underwent the red shift by 10 nm. Based on these results, it was proven that cis-platin was bonded to the DNA. FIG. 4 shows the infrared absorption spectrum when DIDS was reacted with cis-platin. When comparing the infrared absorption spectrum of DIDS shown in FIG. 5 and the infrared absorption spectrum of cis-platin shown in FIG. 6, it was found that the peak at 2140 cm$^{-1}$ derived from an N=C=S group disappeared while the absorption peak at 1302 cm$^{-1}$ derived from an N—C=S group newly appeared. Based on these results, it was proven that cis-platin was bonded to DIDS. FIG. 7 shows the infrared absorption spectrum when DIDS was reacted with CONGO RED. FIG. 8 shows the infrared absorption spectrum of CONGO RED. Based on the findings that the peak at 2140 cm$^{-1}$ derived from an N=C=S group of DIDS disappeared while the thiourea bond peaks at 1645 and 1545 cm$^{-1}$ were intensified, it was proven that DIDS was bonded to CONGO RED. Also based on the overall spectrum shown in FIG. 9 indicating that the peak at 2140 cm$^{-1}$ derived from an N=C=S group of DIDS disappeared while the thiourea bond peaks at 1645 and 1545 cm$^{-1}$ were intensified, the crosslinked construct (A-1) represented by Formula 6 was proven to be formed.

To purify the crosslinked construct thus synthesized, ethanol precipitation was conducted. 200 μl of the reaction solution was taken out into a sample tube, and 20 μl of a 3 mol/l aqueous solution of sodium acetate and 400 μl of ethanol were added to and mixed thoroughly with the reaction solution. After being allowed to stand at room temperature for 1 hour, the mixture was centrifuged at 4° C. and 13,200 rpm for 30 minutes to separate the supernatant and the pellet. The pellet recovered was dissolved again in 10 μl of super-pure water. A drop of this aqueous solution was added by a microsyringe onto the gold electrode formed on a glass substrate with the electrode distance of 10 μm, and dried under nitrogen atmosphere overnight. As a result, a thin film of the sample was formed on the gold electrode.

Figure 10:
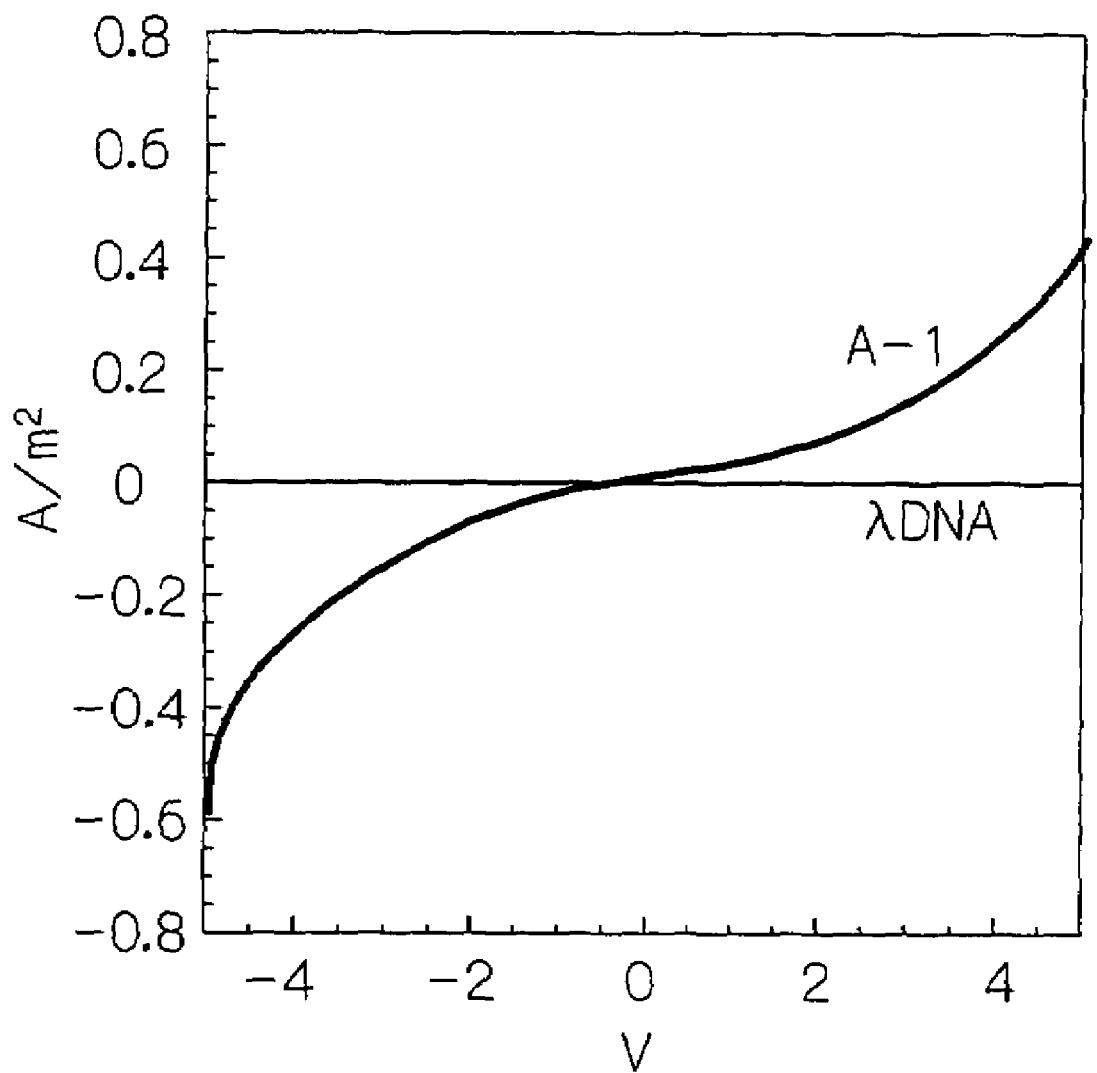
FIG. 10 is a graph showing the relationship of the current density-voltage characteristic of the crosslinked construct (A-1).

The current-voltage characteristic of this sample thin film was evaluated. The current-voltage characteristic was measured using pA METER/DC VOLTAGE SOURCE 4140B (current detection sensitivity of $10^{-12}$ A) manufactured by Hewlett Packard. The results are shown in FIG. 10. The λDNA exhibited no detectable current, showing a resistance of 10 G Ω or higher. On the other hand, the crosslinked construct showed 0.1 A/m² (5×10⁻¹ S/m) at 2 V, indicating an improved DNA conductivity according to the present method.

Example 2

Figure 11:
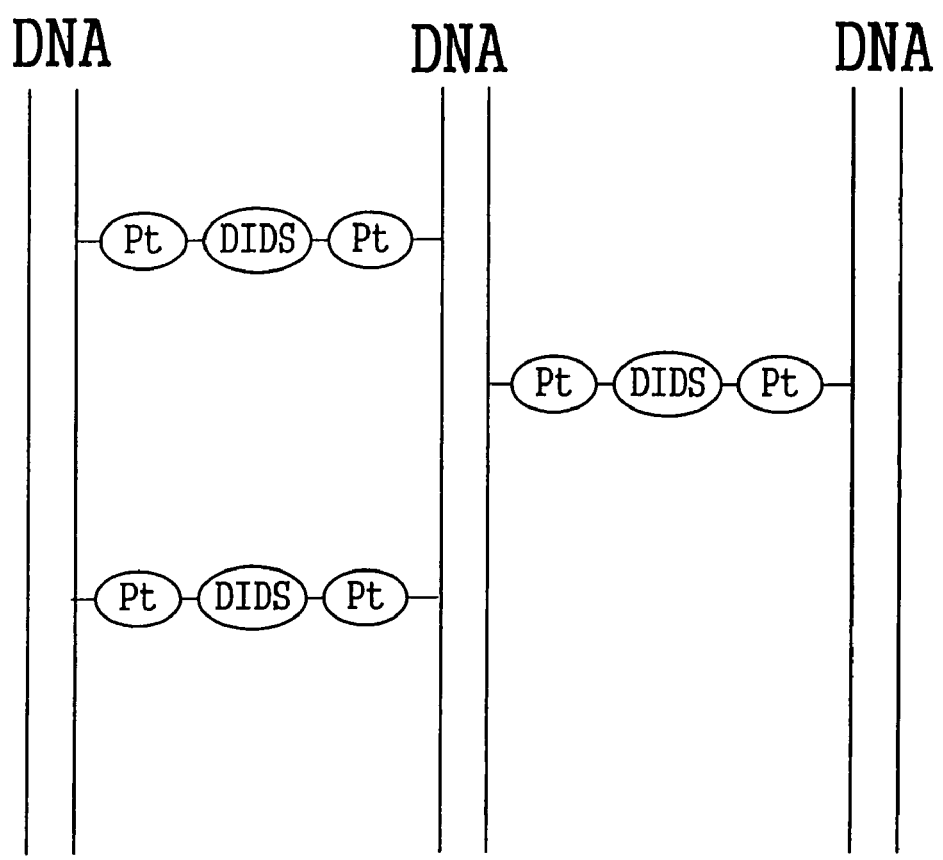
FIG. 11 is a diagram showing the structure of the crosslinked construct (A-2).
Figure 11:
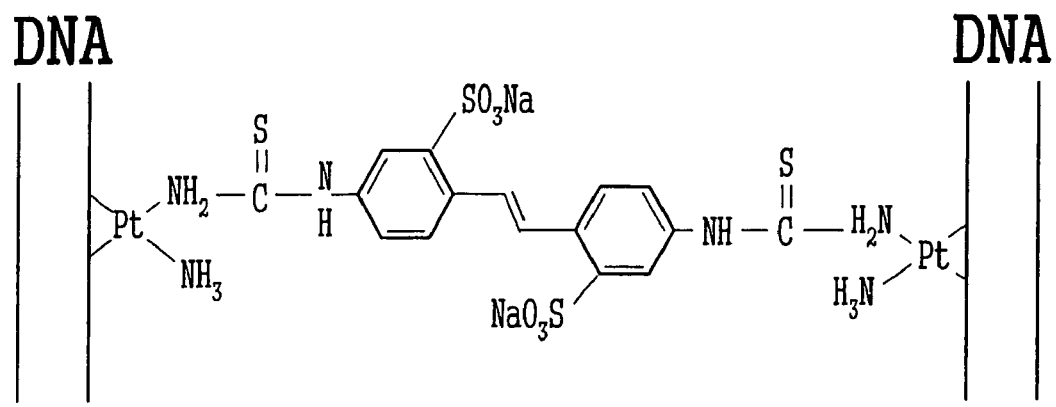
Figure 12:
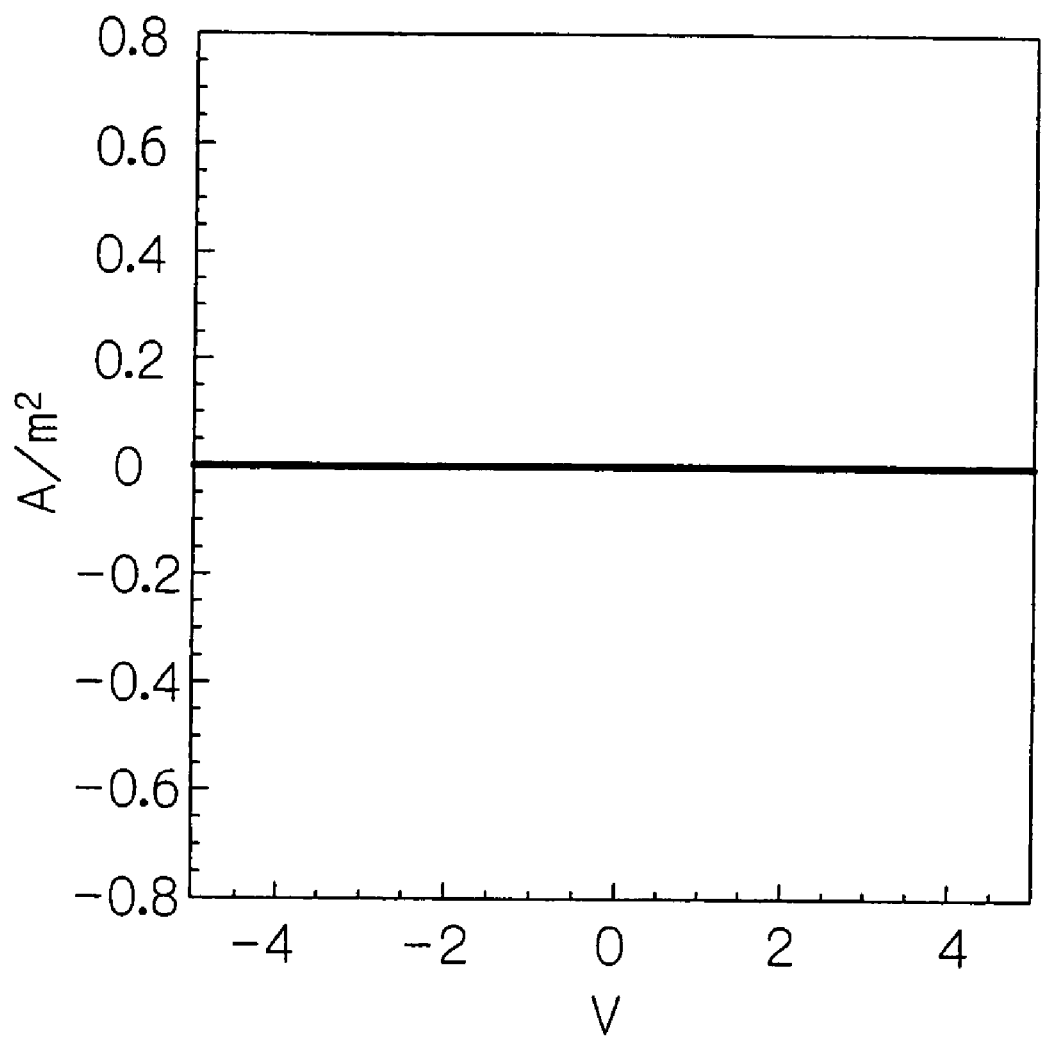
FIG. 12 is a graph showing the relationship of the current density-voltage characteristic of the crosslinked construct (A-2).
Figure 13:
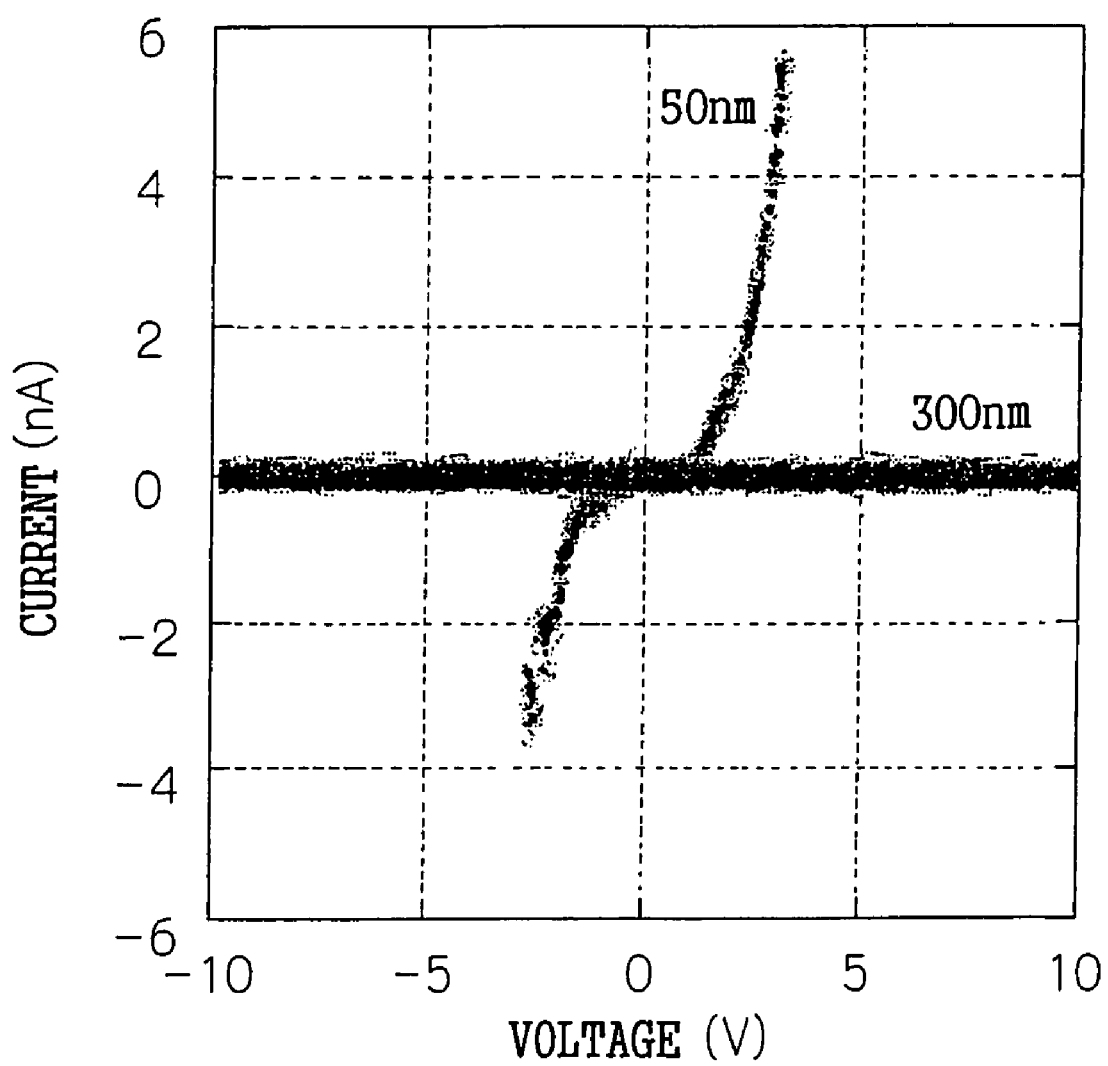
FIG. 13 is a graph showing the relationship of the current-voltage characteristic of the crosslinked construct (A-2).
Figure 14:
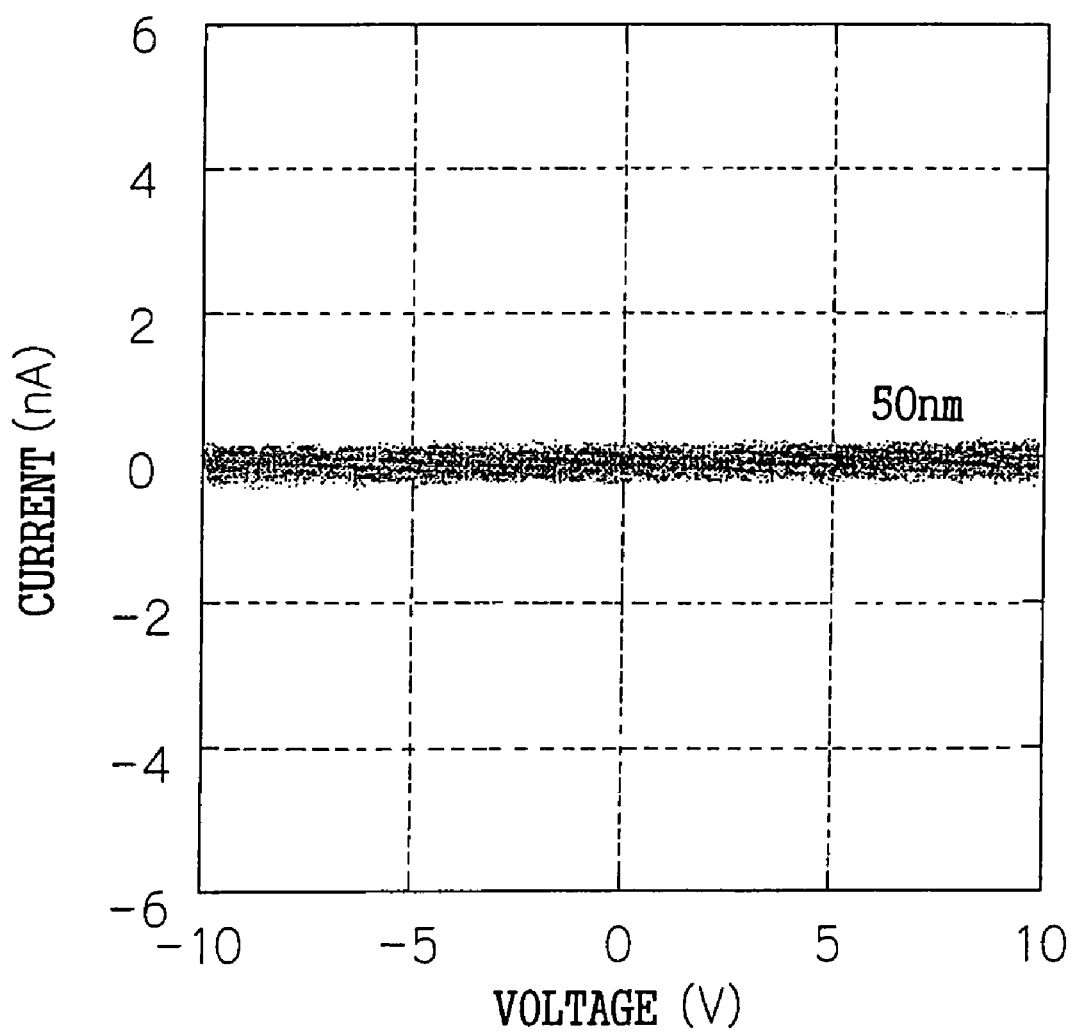
FIG. 14 is a graph showing the current-voltage characteristic of λDNA.

400 µl of a 0.32 mg/ml λ DNA buffer solution was mixed thoroughly with 12 µl of a 5 mg/ml aqueous solution of cis-platin and 300 µl of a 1 mg/ml aqueous solution of DIDS, and kept at 55° C. for 3 days. Similarly to Example 1, the crosslinked construct (A-2) shown in FIG. 11 was confirmed to be generated based on the UV and visible absorption spectrum and infrared absorption spectrum. To purify the crosslinked construct thus synthesized, ethanol precipitation was conducted. 200 µl of the reaction solution was taken out into a sample tube, and 20 µl of a 3 mol/l aqueous solution of sodium acetate and 400 µl of ethanol were added to and mixed thoroughly with the reaction solution. After being allowed to stand at room temperature for 1 hour, the mixture was centrifuged at 4° C. and 13,200 rpm for 30 minutes to separate the supernatant and the pellet. The pellet recovered was dissolved again in 10 µl of super-pure water. A drop of this aqueous solution was added by a microsyringe onto the gold electrode formed on a glass substrate with the electrode distance of 10 µm, and dried under nitrogen atmosphere overnight. As a result, a thin film of the sample was formed on the gold electrode. The current-voltage characteristic was evaluated, and the results obtained are shown in FIG. 12. However, the crosslinked construct synthesized here gave no detectable current with the electrode distance of 10 µm, showing a resistance of 10 G Ω or higher. Accordingly, the electrode distance was reduced and then the current-voltage characteristic was measured. The measurement was conducted employing Dual Probe AFM (Japanese Patent Application No. 2001-006284). The results are shown in FIG. 13. As a result, when the electrode distance was reduced to about 50 nm, a current of about 4 nA was detected at 3 V. As shown in FIG. 14, a naturally occurring λDNA allows no current to be detected even with the electrode distance of 50 nm, suggesting that this method can impart a DNA with a conductivity within 50 nm.

Example 3

Four single-stranded DNAs (hereinafter referred to as ssDNAs) of 120 bases represented by SEQ. ID. Nos. 1 to 4 were designated ssDNA1 to ssDNA4, respectively, each of which was synthesized by a phosphoramidite method using a DNA synthesizer Expedite 8909 manufactured by Applied Biosystems. There was complementarity of the base sequence between ssDNA1 and ssDNA2 and between ssDNA3 and ssDNA4, and a double-stranded DNA can be formed via hydrogen bonds by hybridization. The hybridization was effected by mixing respective ssDNAs at the molar ratio of 1:1 and the resultant mixture was kept at 97° C. for 5 minutes and then cooled to room temperature slowly. After forming a double-stranded DNA by the hybridization, ethanol precipitation was conducted for purification. A double-stranded DNA formed from ssDNA1 and ssDNA2 was designated G0, while a double-stranded DNA formed from ssDNA3 and ssDNA4 was designated G100. All regions other than the regions of 10 base pairs from the both terminals of G0 consisted of adenine-thymine base pairs. On the other hand, all region other than the regions of 10 base pairs from the both terminals of G100 consisted of guanine-cytosine base pairs. Using G100 and G0, a crosslinked construct similar to that in Example 1 was synthesized by the following procedure. 1 ml of a 0.4 mg/ml double-stranded DNA buffer solution was mixed with 80 µl of a 2.5 mg/ml aqueous solution of cis-platinum (II) diamine dichloride. Then 301 µl of a 1 mg/ml aqueous solution of DIDS and 400 µl of a 0.5 mg/ml aqueous solution of CONGO RED were added to the mixture, and the resultant mixture was kept at 55° C. for 3 days. 200 µl of the reaction solution was taken out into a sample tube, and 20 µl of a 3 mol/l aqueous solution of sodium acetate and 400 µl of ethanol were added to and mixed thoroughly with the reaction solution. After being allowed to stand at room temperature for 1 hour, the mixture was centrifuged at 4° C. and 13,200 rpm for 30 minutes to remove the supernatant and recover the pellet. To purify the crosslinked construct thus synthesized, ethanol precipitation was conducted. 200 µl of the reaction solution was taken out into a sample tube, and 20 µl of a 3 mol/l aqueous solution of sodium acetate and 400 µl of ethanol were added to and mixed thoroughly with the reaction solution. After being allowed to stand at room temperature for 1 hour, the mixture was centrifuged at 4° C. and 13,200 rpm for 30 minutes to separate the supernatant and the pellet. The pellet recovered was dissolved again in 10 µl of super-pure water. A drop of this aqueous solution was added by a microsyringe onto the gold electrode formed on a glass substrate with the electrode distance of 10 µm, and dried under nitrogen atmosphere overnight. As a result, a thin film of the sample was formed on the gold electrode.

SEQ. ID. No.: 1

Length of sequence: 120

Type of sequence: Nucleic acid

Strandedness: Single-stranded

Topology: Linear

Molecular type: Synthesized DNA

Sequence Description:

```
CACTGCATAT AAAAAAAAAA AAAAAAAAAA AAAAAAAAAA
AAAAAAAAAA AAAAAAAAAA 60

AAAAAAAAAA AAAAAAAAAA AAAAAAAAAA AAAAAAAAAA
AAAAAAAAAA CAATCGTATC 120
```

SEQ. ID. No.: 2

Length of sequence: 120

Type of sequence: Nucleic acid

Strandedness: Single-stranded

Topology: Linear

Molecular type: Synthesized DNA

Sequence Description:

```
GATACGATTG TTTTTTTTTT TTTTTTTTTT TTTTTTTTTT
TTTTTTTTTT TTTTTTTTTT 60

TTTTTTTTTT TTTTTTTTTT TTTTTTTTTT TTTTTTTTTT
TTTTTTTTTT ATATGCAGTG 120
```

SEQ. ID. No.: 3

Length of sequence: 120

Type of sequence: Nucleic acid

Strandedness: Single-stranded

Topology: Linear

Molecular type: Synthesized DNA

Sequence Description:

```
CACTGCATAT GGGGGGGGGG GGGGGGGGGG GGGGGGGGGG
GGGGGGGGGG GGGGGGGGGG 60

GGGGGGGGGG GGGGGGGGGG GGGGGGGGGG GGGGCGGGGG
GGGGGGGGGG CAATCGTATC 120
```

SEQ. ID. No.: 4

Length of sequence: 120

Type of sequence: Nucleic acid

Strandedness: Single-stranded

Topology: Linear

Molecular type: Synthesized DNA

Sequence Description:

```
GATACGATTG CCCCCCCCCC CCCCCCCCCC CCCCCCCCCC
CCCCCCCCCC CCCCCCCCCC 60

CCCCCCCCCC CCCCCCCCCC CCCCCCCCCC CCCCCCCCCC
CCCCCCCCCC ATATGCAGTG 120
```

Figure 15:
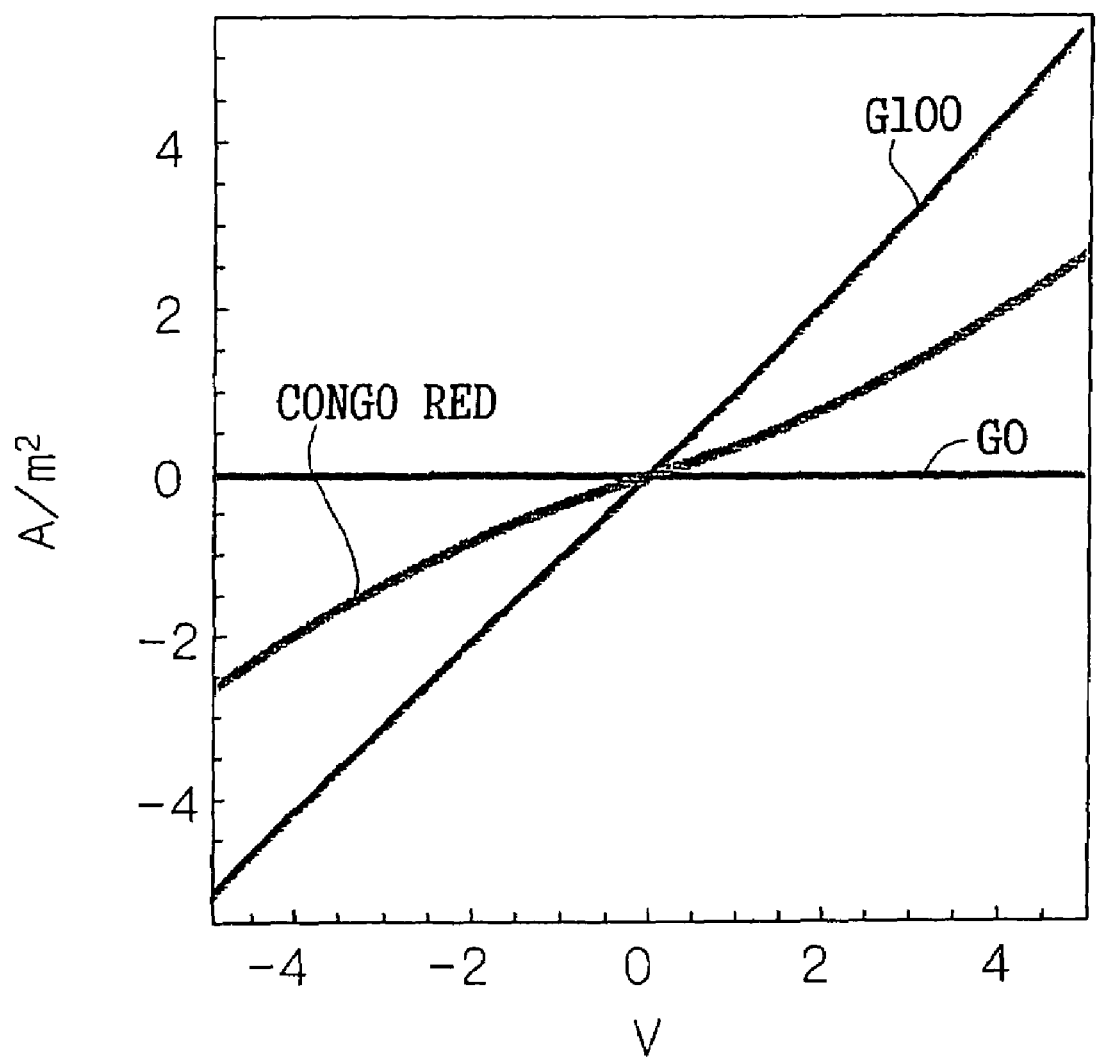
FIG. 15 is a graph showing the current density-voltage characteristic of G100 crosslinked construct and G crosslinked construct.
Figure 16:
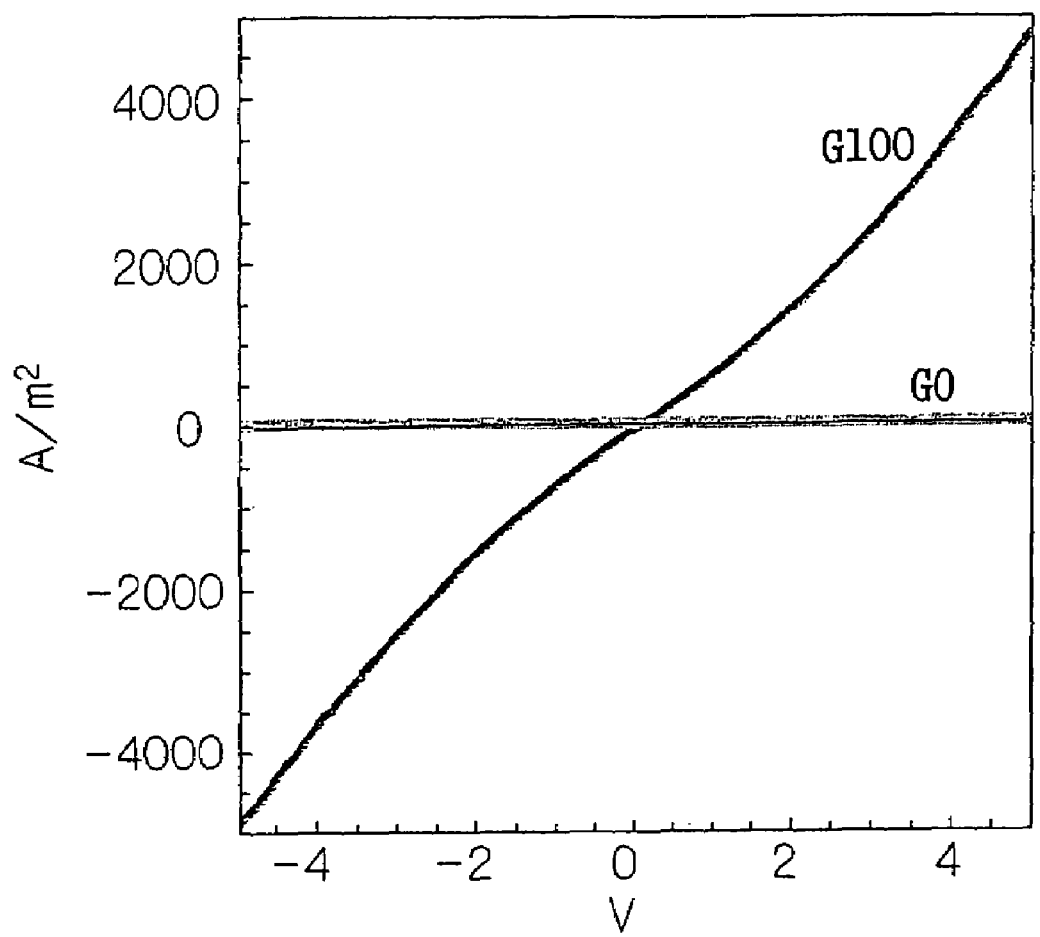
FIG. 16 is a graph showing the current density-voltage characteristic of G100 crosslinked construct and G0 crosslinked construct.
Figure 17:
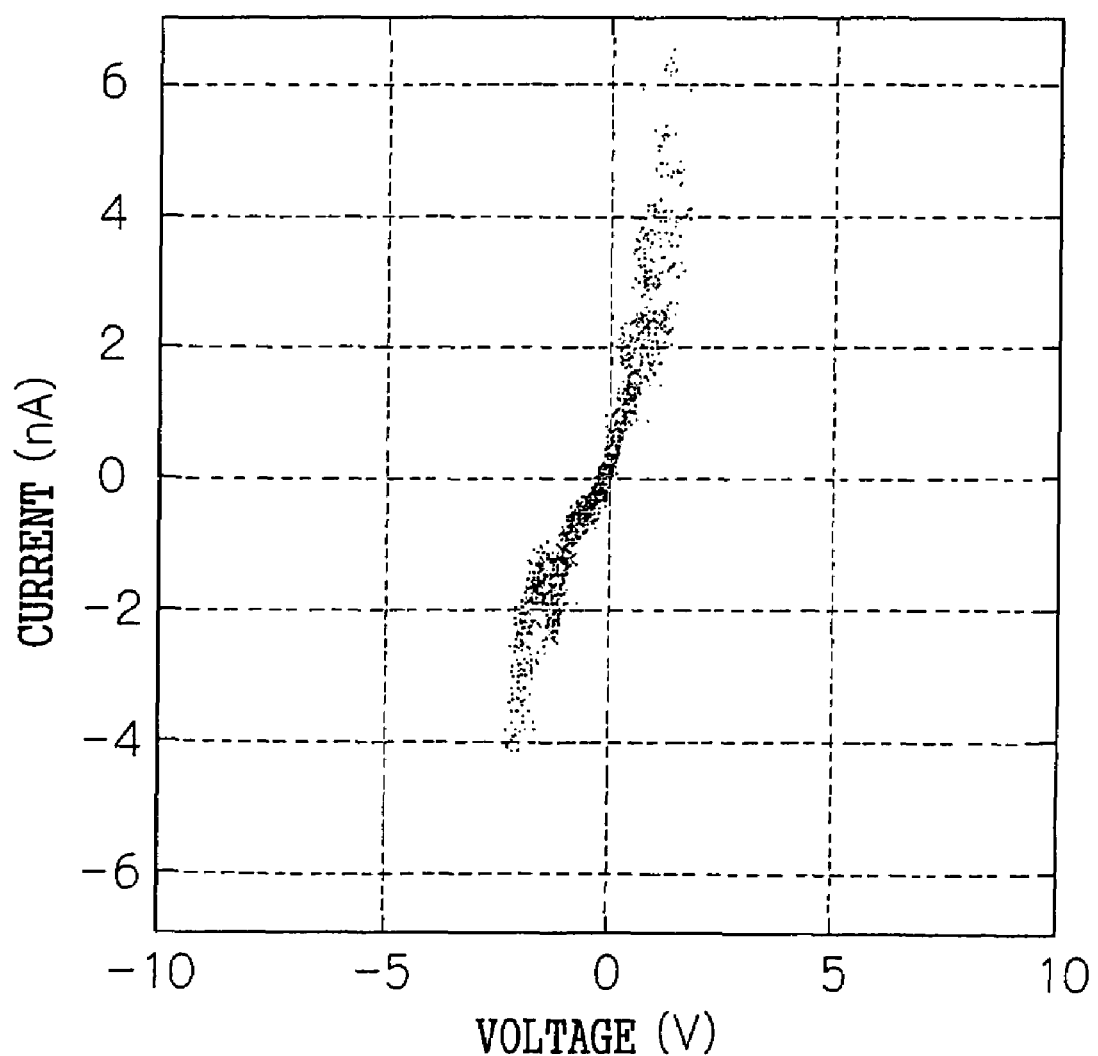
FIG. 17 is a graph showing the current-voltage characteristic of G100 crosslinked construct.
Figure 18:
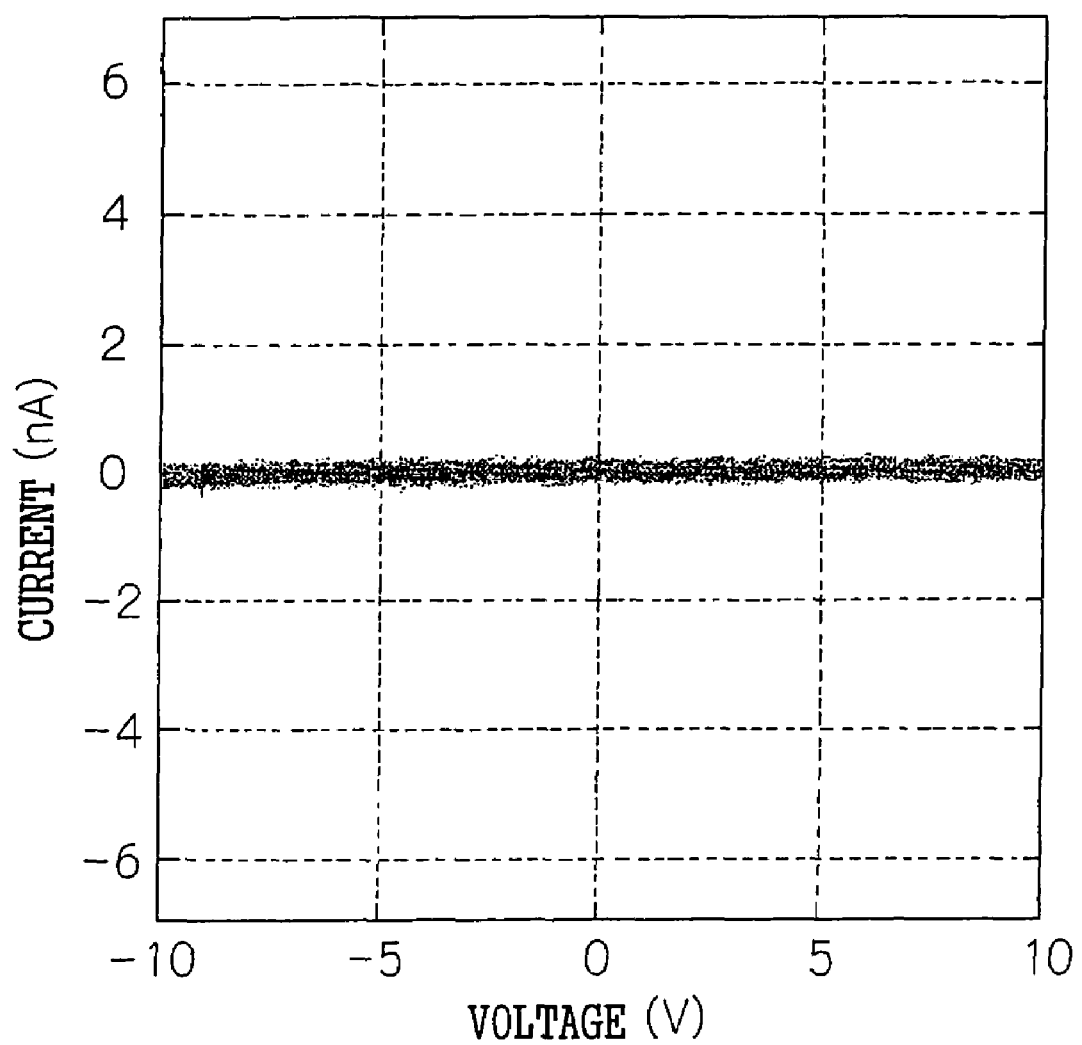
FIG. 18 is a graph showing the current-voltage characteristic of G0 crosslinked construct.

The results of the evaluation of the current-voltage characteristics of G100 crosslinked construct and G0 crosslinked construct are shown in FIGS. 15 and 16. When the electrode distance was 10 μm, G0 crosslinked construct gave no detectable current, while G100 crosslinked construct gave 4 A/m$^2$ (10 S/m) at 4 V (FIG. 15) with the maximum level of 3800 A/m$^2$ (10$^4$ S/m) being given at 4 V (FIG. 16). The current-voltage characteristic of G100 crosslinked construct by Dual Probe AFM is shown in FIG. 17. G100 crosslinked construct gave 5 nA at 1 V with the electrode distance of 500 nm. The current-voltage characteristic of G0 crosslinked construct by Dual Probe AFM is shown in FIG. 18. G0 crosslinked construct gave no detectable current even with the electrode distance of 150 nm.

Comparative Example 1

Figure 19:
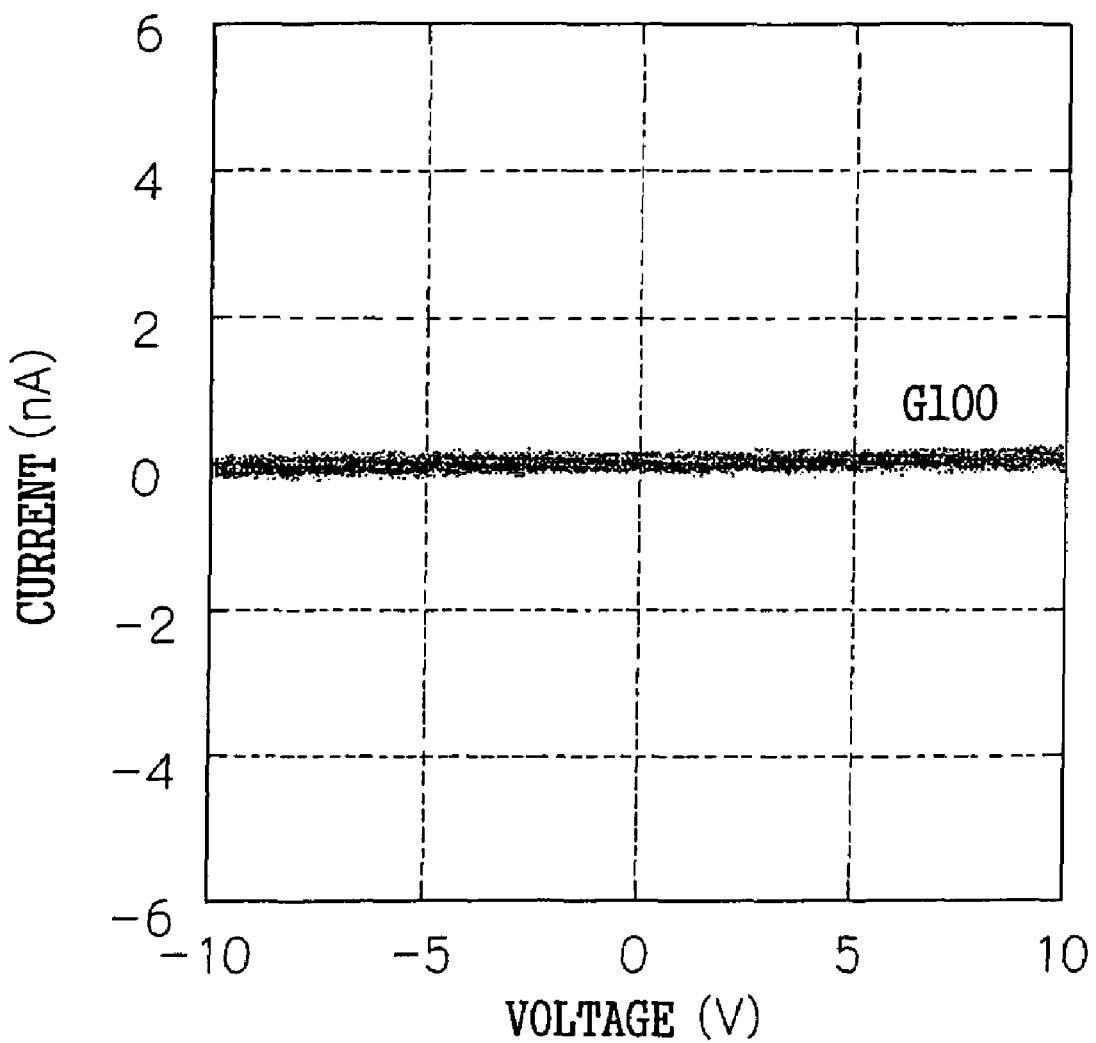
FIG. 19 is a graph showing the current-voltage characteristic of G100-cis-platin.
Figure 20:
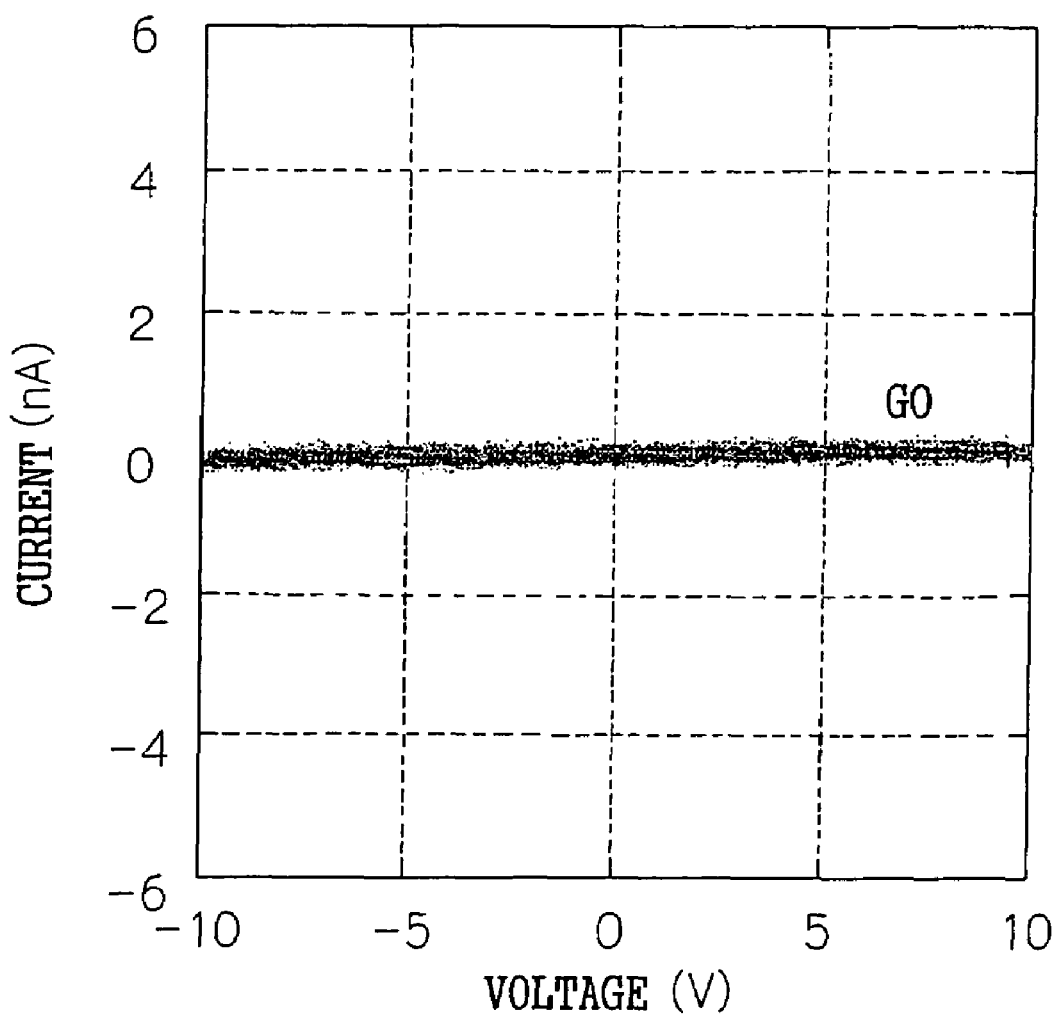
FIG. 20 is a graph showing the current-voltage characteristic of G0-cis-platin.

Cis-platin was added to the double-stranded DNA G0 and G100 synthesized in Example 3 by the following procedure. 1 ml of a 0.4 mg/ml double-stranded DNA buffer solution was mixed with 80 μl of a 2.5 mg/ml aqueous solution of cis-platin, and the mixture was kept at 55° C. for 3 days. For the purification, ethanol precipitation was conducted. 200 μl of the reaction solution was taken out into a sample tube, and 20 μl of a 3 mol/l aqueous solution of sodium acetate and 400 μl of ethanol were added to and mixed thoroughly with the reaction solution. After being allowed to stand at room temperature for 1 hour, the mixture was centrifuged at 4° C. and 13,200 rpm for 30 minutes to remove the supernatant and recover the pellet. Similarly to Example 1, cis-platin was proven to be added to the DNA on the basis of the UV and visible light absorption spectrum. The results of the evaluation of the current-voltage characteristic using Dual Probe AFM are shown in FIGS. 19 and 20. As a result, no detectable current was obtained simply by adding cis-platin to G100 and G0, and it was found that the product had a resistance of 10 GΩ or higher.

Example 4

Figure 21:
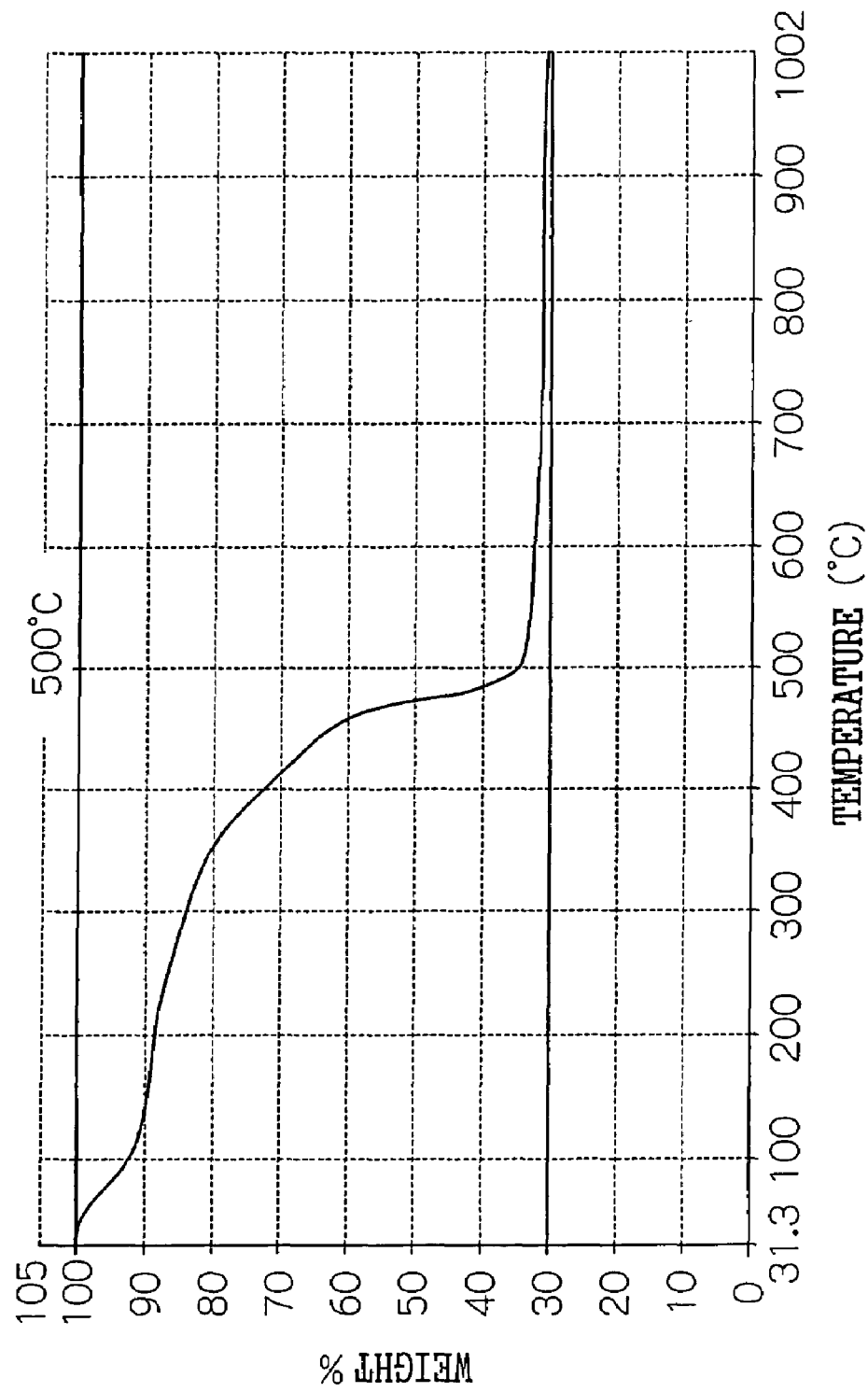
FIG. 21 is a graph showing the thermogravimetric curve of the reaction product of a DNA, cis-platin, DIDS and CONGO RED.
Figure 22:
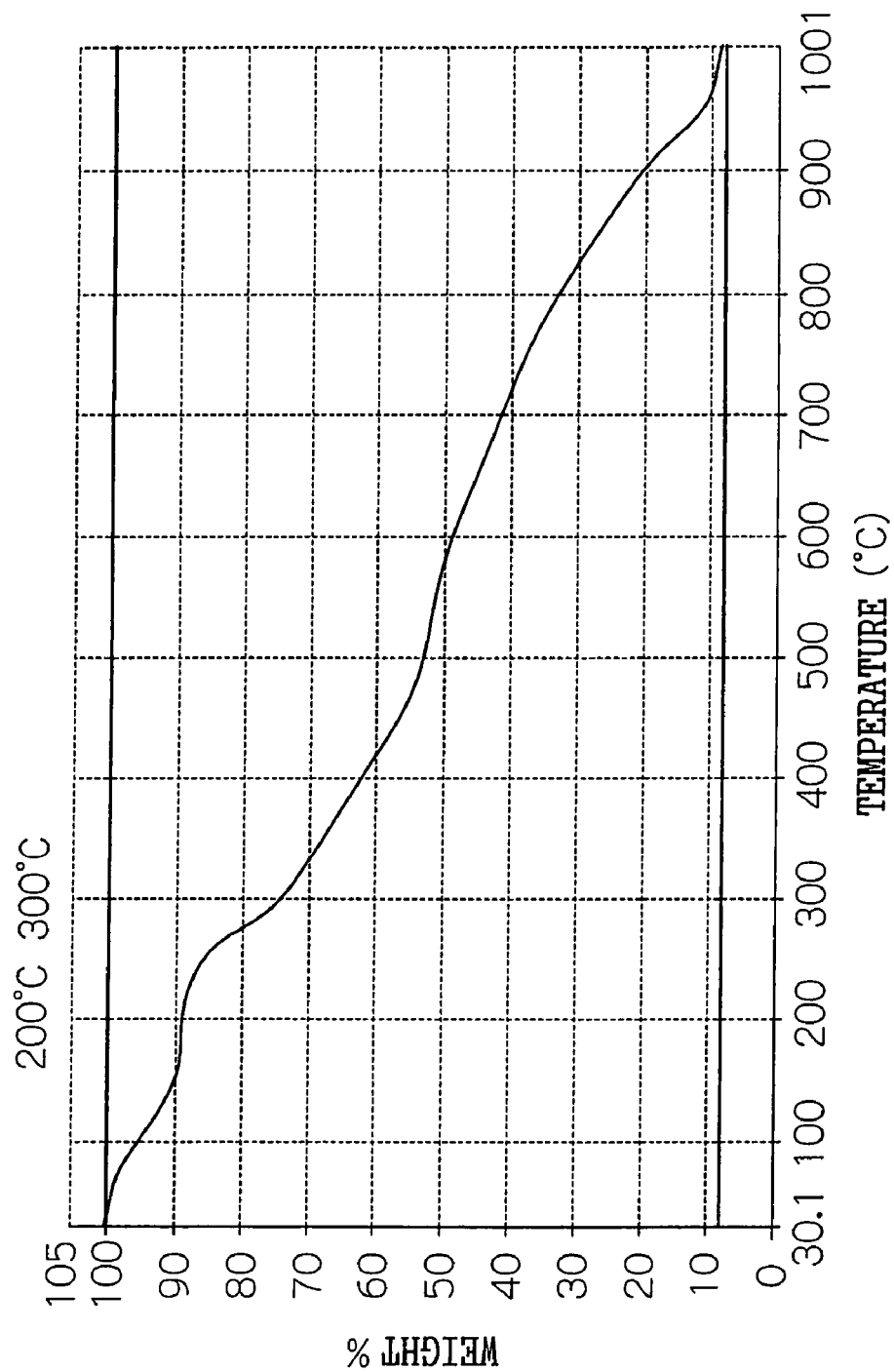
FIG. 22 is a graph showing the thermogravimetric curve of a DNA.

A DNA isolated from salmon sperm (Wako Pure Chemical Industries, Ltd.) was employed. First, the purification was conducted by ethanol precipitation. 200 μl of a 2 mg/ml DNA TE buffer solution was taken out into a sample tube, and 20 μl of a 3 mol/l aqueous solution of sodium acetate and 400 μl of ethanol were added to and mixed thoroughly with the buffer solution. After being allowed to stand at room temperature for 1 hour, the mixture was centrifuged at 4° C. and 13,200 rpm for 30 minutes to remove the supernatant. 200 μl of 70% ethanol was added to the remaining pellet, and the mixture was centrifuged at 4° C. and 13,200 rpm again for 5 minutes to remove the supernatant and recover the precipitating purified DNA. 5.6 ml of a 2 mg/ml aqueous solution of purified DNA was mixed throughly with 2.24 ml of a 2.5 mg/ml aqueous solution of cis-platinum (II) diamine dichloride and 2.24 ml of a 1 mg/ml aqueous solution of DIDS and the mixture was kept at 55° C. for 3 days. 200 μl of the reaction solution was taken out into a sample tube, and 20 μl of a 3 mol/l aqueous solution of sodium acetate and 400 μl of ethanol were added to and mixed thoroughly with the reaction solution. After being allowed to stand at room temperature for 1 hour, the mixture was centrifuged at 4° C. and 13,200 rpm for 30 minutes to remove the supernatant and recover the pellet. The thermal decomposition temperature of the crosslinked construct thus synthesized was determined using a Perkin Elmer thermal analyzer TGA-7. The resultant thermogravimetric curve is shown in FIG. 21. The thermal decomposition temperature was found to be 450° C. On the other hand, the thermal decomposition temperature of the DNA was 250° C. as shown in FIG. 22.

Example 5

Figure 23:
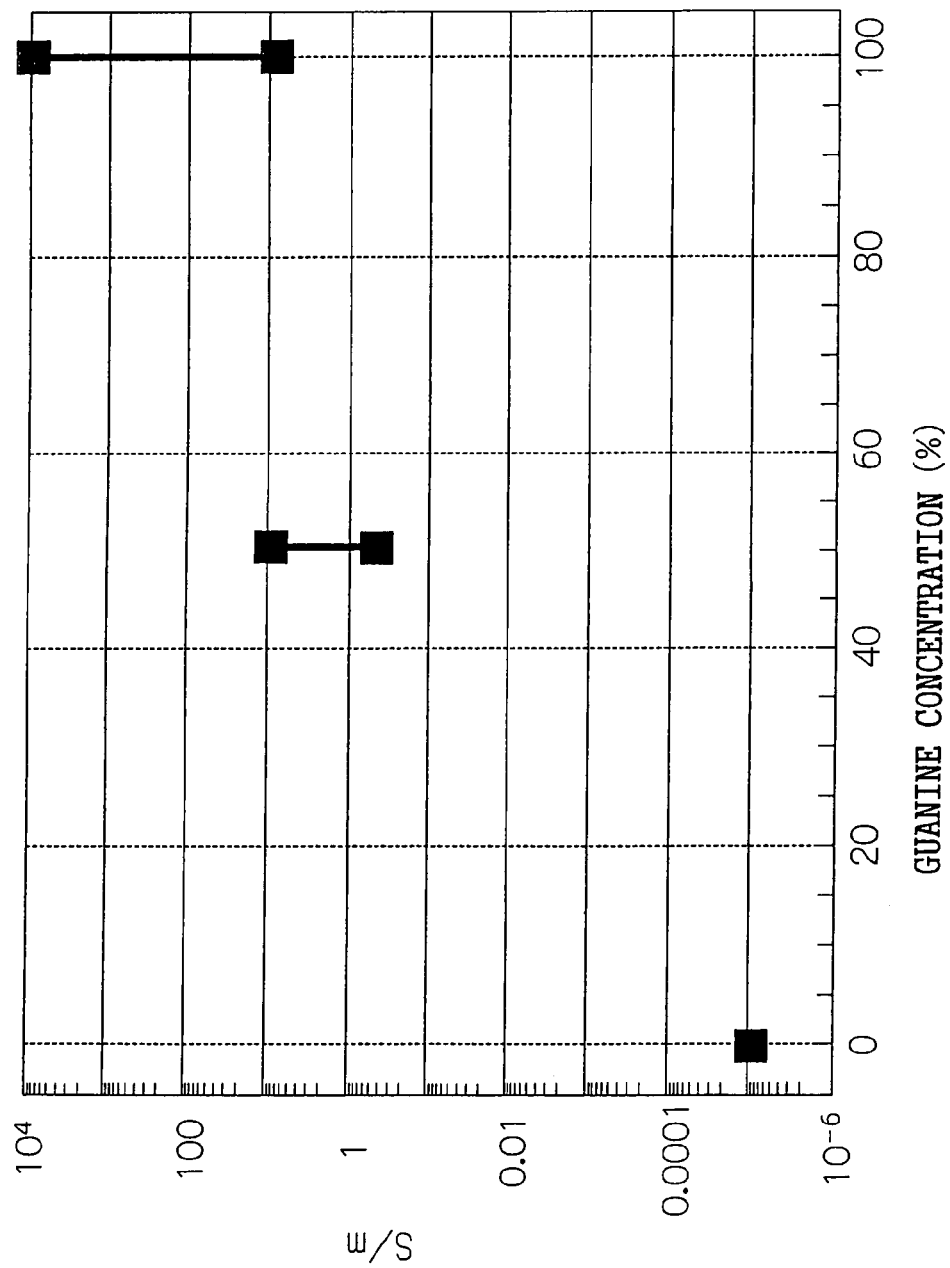
FIG. 23 is a graph showing the relationship between the guanine concentration and the current.

The currents of the crosslinked construct in Example 1, G100 and G0 in Example 3 were compared with each other by the method employed in Example 1. The results are shown in FIG. 23. The point at the bottom on the left represents the result of G0 in Example 3, the middle line represents the result of the crosslinked construct in Example 1 and the line at the top on the right represents the result of G100 in Example 3. Based on this figure, we found that the current was increased in response to the concentration of guanine in a DNA.

What is claimed is:

1. An electronic device, comprising:
    an organic conductor comprising a deoxyribonucleic acid (DNA) strand and an electric charge-donating material bonded to the deoxyribonucleic acid (DNA) strand,
    wherein the electric charge-donating material comprises an electric charge-transfer substance that bonds to a base of the DNA strand, and an electric charge-generating substance bonded to the electric charge-transfer substance via a crosslinking agent; and
    wherein the electric charge-transfer substance, is cis-platinum (II) diamine dichioride, and the electric charge-generating substance is an amine compound.

2. The electronic device of claim 1, further comprising a substrate onto which the organic conductor is applied.

3. An electronic material enabling a supply of electricity, comprising:
    an organic conductor comprising a deoxyribonucleic acid (DNA) strand; and an electric charge-donating material bonded to the deoxyribonucleic acid (DNA) strand,
    wherein the electric charge-donating material comprises an electric charge-transfer substance, that bonds to a base of the DNA strand, and an electric charge-generating substance bonded to the electric charge-transfer substance via a crosslinking agent, and
    wherein the electric charge-transfer substance is cis-platinum (II) diamine dichioride, and the electric charge-generating substance is an amine compound.

4. The electronic device according to claim 1, wherein the electric charge-generating substance is selected from the group consisting of CONGO RED, an azine dye indicator, pararosanilin and thionine.

5. The electronic material enabling a supply of electricity according to claim 3, wherein the electric charge-generating substance is selected from the group consisting of CONGO RED, an azine dye indicator, pararosanilin and thionine.

* * * * *

SEQUENCE LISTING

<160> NUMBER OF SEQ ID NOS: 4

<210> SEQ ID NO 1
<211> LENGTH: 120
<212> TYPE: DNA
<213> ORGANISM: Artificial Sequence
<220> FEATURE:

-continued

```
<223> OTHER INFORMATION: Primer

<400> SEQUENCE: 1
cactgcatat aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa caatcgtatc     120

<210> SEQ ID NO 2
<211> LENGTH: 120
<212> TYPE: DNA
<213> ORGANISM: Artificial Sequence
<220> FEATURE:
<223> OTHER INFORMATION: Primer

<400> SEQUENCE: 2
gatacgattg tttttttttt tttttttttt tttttttttt tttttttttt tttttttttt      60
tttttttttt tttttttttt tttttttttt tttttttttt tttttttttt atatgcagtg     120

<210> SEQ ID NO 3
<211> LENGTH: 120
<212> TYPE: DNA
<213> ORGANISM: Artificial Sequence
<220> FEATURE:
<223> OTHER INFORMATION: Primer

<400> SEQUENCE: 3
cactgcatat gggggggggg gggggggggg gggggggggg gggggggggg gggggggggg      60
gggggggggg gggggggggg gggggggggg gggggggggg gggggggggg caatcgtatc     120

<210> SEQ ID NO 4
<211> LENGTH: 120
<212> TYPE: DNA
<213> ORGANISM: Artificial Sequence
<220> FEATURE:
<223> OTHER INFORMATION: Primer

<400> SEQUENCE: 4
gatacgattg cccccccccc cccccccccc cccccccccc cccccccccc cccccccccc      60
cccccccccc cccccccccc cccccccccc cccccccccc cccccccccc atatgcagtg     120
```